(12) United States Patent
Wang

(10) Patent No.: US 9,243,242 B2
(45) Date of Patent: *Jan. 26, 2016

(54) METHODS OF MAKING DI-TAGGED DNA LIBRARIES FROM DNA OR RNA USING DOUBLE-TAGGED OLIGONUCLEOTIDES

(71) Applicant: Yan Wang, San Diego, CA (US)

(72) Inventor: Yan Wang, San Diego, CA (US)

(*) Notice: Subject to any disclaimer, the term of this patent is extended or adjusted under 35 U.S.C. 154(b) by 132 days.

This patent is subject to a terminal disclaimer.

(21) Appl. No.: 14/226,321

(22) Filed: Mar. 26, 2014

(65) Prior Publication Data

US 2014/0206581 A1     Jul. 24, 2014

Related U.S. Application Data

(60) Division of application No. 13/491,516, filed on Jun. 7, 2012, now Pat. No. 8,722,585, which is a continuation-in-part of application No. 13/466,610, filed on May 8, 2012, now abandoned.

(60) Provisional application No. 61/483,710, filed on May 8, 2011.

(51) Int. Cl.
| | |
|---|---|
| C12N 15/10 | (2006.01) |
| C12N 15/65 | (2006.01) |
| C12N 15/66 | (2006.01) |
| C12Q 1/68 | (2006.01) |

(52) U.S. Cl.
CPC ............ *C12N 15/1065* (2013.01); *C12N 15/65* (2013.01); *C12N 15/66* (2013.01); *C12Q 1/6806* (2013.01); *C12Q 1/6855* (2013.01); *C12Q 1/6869* (2013.01)

(58) Field of Classification Search
CPC .......................... C12N 15/1065; C12N 15/66
See application file for complete search history.

*Primary Examiner* — Larry Riggs
*Assistant Examiner* — Karla Dines
(74) *Attorney, Agent, or Firm* — Lili Chen

(57) ABSTRACT

Disclosed are methods, compositions and kits related to making double-tagged DNA libraries from RNA/DNA samples. A double-tagged oligonucleotide (DTO) is employed to efficiently add two different tags to ends of DNAs to make a double-tagged DNA libraries. Also disclosed are methods to make mate pair libraries using the double-tagged oligonucleotide, and methods to make double-tagged single stranded DNA. The double-tagged DNA libraries of the invention are ready to be used on next generation sequencing machines.

4 Claims, 11 Drawing Sheets

C18 hexa-ethyleneglycol spacer.

C9 triethylene glycol spacer 9 atom photo-cleavable spacer (PC spacer)

C3 phosphoramidite spacer

METHODS OF MAKING DI-TAGGED DNA LIBRARIES FROM DNA OR RNA USING DOUBLE-TAGGED OLIGONUCLEOTIDES

CROSS-REFERENCE TO RELATED APPLICATIONS

This application is a division of U.S. application Ser. No. 13/491,516, filed Jun. 7, 2012, which is a continuation-in-part of U.S. application Ser. No. 13/466,610, filed May 8, 2012, now abandoned, which claims the benefit of U.S. provisional patent application No. 61/483,710, filed May 8, 2011, the contents of which are herein incorporated by reference in their entirety.

BACKGROUND OF THE INVENTION

1. Field of the Invention

The present invention provides methods, compositions and kits related to making double-tagged DNA libraries using a double-tagged oligonucleotide. It particularly relates to methods, compositions and kits for making di-tagged dsDNA libraries suitable for high throughput sequencing from DNA and RNA samples.

2. Description of the Related Art

Next Generation Sequencing (NGS) is a high-throughput sequencing technology that performs thousands or millions of sequencing in parallel. The NGS technology enables researchers to answer fundamental biological questions at a genomic scale and has great potential in medical applications. The first step to apply NGS technologies is constructing DNA libraries of random DNA fragments generated from DNA/RNA samples, having different sequence tags attached at both ends. Preparation of high quality di-tagged DNA library is critical for successful sequencing.

As Next Generation Sequencing technologies evolve and advance, there are growing demands for PCR free library preparation, Mate Pair library preparation and single stranded library preparation to serve researchers with specific project needs. The challenges of PCR free library preparation is the ligation step: current method involves ligating two different sequence tags to blunt ended DNA fragments using a DNA ligase. Due to random ligation of different tags to ends of DNA fragments, ligation products include DNA sequences with only one tag, with the same tags, or with two different tags. PCR amplification is needed to selectively amplify the DNA fragments having different tags. An improved ligation method uses one "Y" shaped tag having a non-complementary outer portion and a complementary inner portion. Two strands of the non-complementary outer portion have different sequence tags, and two strands of the complementary inner portion anneal to each other to form a dsDNA that can be ligated to dsDNA fragments. Once a DNA is ligated to two "Y" shaped tags, each DNA strand will be ligated to different sequence tags of the non-complementary outer portion. However, selective PCR amplification is still needed since this method does not exclude the possibility that DNA is ligated to only one "Y" shaped tag.

Using a double-tagged oligonucleotide, the present invention provides a method of making a di-tagged DNA without the need of performing a PCR, therefore eliminating the sequence bias caused by PCR.

A mate pair DNA refers to a DNA sequence comprising two DNA segments originally located long distance apart in the genome. A mate pair library is comprised of mate pair DNA sequences with two different sequence tags attached at the ends. Mate pair sequencing is useful for many applications such as genomic sequence assembly, assessment of genomic rearrangement, and assembly of repetitive sequences. To make a mate pair library, end sequences of a large DNA fragment are connected together and attached to two different sequence tags. Current techniques for preparing mate pair DNA libraries involve fragmenting genomic DNA into large fragments, performing end repairs, labeling ends of large DNA fragments with biotin, self-ligation of biotinylated ends, random fragmentation to generate smaller DNA fragments, isolation of biotinylated fragments, performing end repairs, and ligation of two different tags to the DNA fragments. This procedure comprises many enzymatic and cleaning steps leading to low yield of mate pair DNAs. The low ligation efficiency of biotinylated nucleotides further limits the application of this method.

Using a double-tagged oligonucleotide, the present invention provides a method of making Mate-Pair DNA libraries with less enzyme reactions and less purification steps, resulting in simpler workflow and better recovery.

Single stranded DNA library has many applications such as DNA methylation analysis and hybridization based target capture. Existing method for generating single stranded DNA involves ligation of an adaptor to a dsDNA molecule, and uses only one primer to linearly amplify one single strand. One of the major drawbacks for this method is the sequence bias introduced by PCR cycles.

Using a double-tagged oligonucleotide, the present invention provides a simple PCR-free method to generate single stranded DNA library from dsDNA, eliminating the sequence bias caused by PCR. The resulting library would well reflect the complexity and composition of the DNA sequences of the starting materials.

RNA sequencing (RNA Seq) uses high throughput sequencing technology for quantifying and mapping transcriptomes, enabling rapid profiling and deep investigation of transcriptional activities. The first step of RNASeq is to convert a population of RNA molecules into a library of DNA molecules with different tags attached to both ends, which can then be sequenced in a high throughput manner. The conventional method for preparing tagged DNAs from RNAs involves reverse transcription to generate first and second complementary DNA (cDNA) strands, DNA fragmentation, DNA ends repairing, adaptor ligation, and PCR amplification. These procedures include multiple enzyme reactions and buffer exchanges between different enzyme reactions, resulting in significant loss of starting materials. Sequence-specific bias may also be introduced during ligation and amplification steps.

Using a single stranded, double-tagged oligonucleotide, the present invention provides a method of making RNA libraries without synthesizing second strand cDNA, resulting not only simpler work flow, but also provides directional information on the RNA Transcripts. More importantly, it offers a library preparation solution to RNA samples of extremely small amounts, such as applications for CLIP Seq.

SUMMARY OF THE INVENTION

The present invention pertains to methods, compositions and kits related to making di-tagged DNA libraries from RNA/DNA sequences, which are suitable for using in high throughput sequencing. The present invention employs a Double-Tagged Oligonucleotide (DTO) to make di-tagged DNAs, allowing efficient addition of different tags to both ends of a DNA sequence.

The present invention provides a DTO that sequentially comprises a pre-selected sequence tag A, a linker, and a pre-selected sequence tag B. The sequence tags A and B are preselected to match sequence tags specific for sequencing platforms. The DTO can be a double stranded DNA oligo used for ligation with two ends of double stranded DNAs to form a circular molecule. The double stranded DTO may have nick(s), gap(s), modified nucleotides, abasic nucleotides, or other chemical moieties in its linker region. The DTO can be a single stranded DNA oligo used as a primer for synthesizing a complementary DNA from a RNA or DNA sequence. The single stranded DTO further comprises a priming sequence at its 3' end.

The linker of the DTO comprises a natural or non-natural nucleotide sequence located between sequence tags A and B, that provides a breaking site or a stopping sequence. A breaking site refers to a region in a DTO that is susceptible to photo, enzymatic, or chemical cleavage. The breaking site may comprise a single-stranded DNA/RNA sequence or a double-stranded DNA sequence with modified nucleotides and/or other non-nucleotide chemical moieties. A stopping sequence refers to modified nucleotides or non-nucleotide chemical moieties that can stop elongation of a DNA during a DNA polymerization reaction.

In some embodiment, the DTO further comprises a priming sequence at its 3' end. The priming sequence is a sequence or a mixture of sequences that is complementary to part of a RNA/DNA sequence and used as a primer for synthesizing a complementary DNA (cDNA). The priming sequence, for example, can be a mixture of random hexamers for annealing to any complementary location of a RNA/DNA sequence or a oligo(dT) for annealing to a 3' end of any RNA with a poly-adenine (poly(A)) tail. The term "complementary DNA" or "cDNA" used herein refers to a single-stranded DNA sequence that is synthesized from and is complementary to a RNA or DNA template. A cDNA complementary to a RNA template can be synthesized using a reverse transcription reaction, and a cDNA complementary to a DNA template can be synthesized using a DNA polymerization reaction.

In one embodiment, the present invention provides a method of making a di-tagged DNA library, comprising the steps of: a) providing a double-tagged oligonucleotide (DTO), sequentially comprising a sequence tag A, a linker, and a sequence tag B; b) providing a DNA or RNA fragment; c) connecting the DTO to the DNA fragment or a cDNA fragment generated from the DNA or RNA fragment to form a circular DNA-DTO molecule; e) generating a linear DNA from the circular DNA-DTO molecule with sequence tag A and tag B at its ends. The collection of such linear DNAs with sequence tag A and tag B forms a di-tagged DNA library. In some embodiment, the linear DNA fragments or free DTOs are digested by exonucleases so that they can be easily separated from the circular DNA-DTO molecules.

The linker of the DTO comprises a stopping sequence or a breaking site. The stopping sequence comprises modified nucleotides or chemical moieties that can stop a DNA polymerization reaction. The stopping sequence may comprise modified nucleotide analogues that cannot form base pairs with natural nucleotides; modified nucleotide analogues that can form base pairs with natural nucleotides, but are structurally incompatible with polymerases; and chemical moieties with little structural similarities to nucleotides that can function to stop DNA polymerization. The breaking site comprises a special region of the DTO that is susceptible to photo, enzymatic or chemical cleavage. The DTO molecule can be a single stranded or a double stranded DNA, which can be connected to DNA fragments or cDNA fragments via ligation, reverse transcription or DNA polymerization. There are two methods for generating a linear DNA from a circular DNA-DTO molecule. If there is a breaking site within the DTO sequence, linear DNAs with sequence tag A and tag B can be generated by breaking at the breaking site. Alternatively, using a primer pair corresponding to sequence tag A and tag B, a PCR is performed to generate a di-tagged linear DNA from the circular DNA-DTO molecule.

In one embodiment, the invention provides a method for making a di-tagged DNA from double stranded DNA sequences. The method comprises the following steps: a, ligate two ends of a double stranded DNA fragment to a double-stranded DTO with a breaking site to make a circular dsDNA; b, use an appropriate method to cleave the circular sequence at the breaking site to generate a linear DNA sequence with two different sequence tags (tag A and tag B) at each end of the sequence. In some embodiment, the breaking site comprises uracil nucleotides, a single stranded DNA, a single-stranded RNA, or a double stranded RNA sequence. In other embodiment, the breaking site comprises a photo-cleavable nucleotide spacer or nucleotide analogs susceptible to chemical cleavage.

In some embodiment, the invention provides a method of making a di-tagged DNA comprises the steps of the following: a, ligate a double-stranded DTO to DNA fragments to form a circular DNA-DTO product; b, use sequence tag A and B as PCR primers to amplify the DNA fragments with sequence tag A and B at both ends.

In one embodiment, the present invention provides a simple and highly efficient method for making mate pair DNA libraries. The method comprises the following steps: a, ligate a double stranded DTO to large DNA fragments to generate large circular DNAs; b, randomly fragment large circular DNAs to small DNA fragments; c, perform end repair of the small DNA fragments to make ready for ligation; d, self-ligate the small DNA fragments to generate small circular DNA; e, perform PCR with the small circular DNA to generate a linear DNA with tags A and B, which contains sequences of both ends from a same large DNA fragment. In some embodiment, the linear DTOs and DNA fragments are digested by exonuclease treatment and are removed from the closed-circular DNA-DTO molecules. In some embodiment, the DTO comprises a breaking site in its linker region. The small circular DNA is cleaved at the breaking site to generate a linear DNA with two sequence tags at the ends. A PCR is performed on the linear DNA to select DNA sequences with two sequence tags. In some embodiment, the DTO comprises a stopping sequence in its linker region.

In some embodiment, the present invention provides a method of making a mate pair DNA libraries from large DNA fragments using a nicked DTO. The method comprises the steps of the following: a, ligate both ends of a large DNA fragment to a double-tagged oligonucleotide to generate a large circular DNA, wherein the double-tagged oligonucleotide has a nick site on each of the opposite strand; b, perform a nick translation to elongate the 3' end of each nick site; c, break the large circular DNA at the nick sites to generate a smaller linear DNA with the double-tagged oligonucleotide; d, end repair the smaller linear DNA to make it ligation ready; e, self-ligate the smaller linear DNA to form a small circular DNA that contains end sequences of a large DNA fragment and double-tagged oligonucleotide; f, perform PCR with the small circular DNA to generate a linear DNA with tags A and B. In some embodiment, the linear DTOs and DNA fragments are digested by exonuclease treatment and are removed from the circular DNA-DTO molecules. In some embodiment, the DTO comprises a breaking site in its linker region. The small circular DNA is cleaved at the breaking site to generate a linear DNA with two sequence tags at the ends. A PCR is performed on the linear DNA to select DNA sequences with two sequence tags.

The invention provides a method for making a di-tagged DNA from a RNA sequence using a single stranded DTO with a priming sequence. The method comprises the following steps: a, annealing the single stranded DTO to the RNA sequence; b, extending the 3' end of the DTO using a reverse transcriptase to make a cDNA-DTO molecule; c, ligating the 3' and 5' ends of the cDNA-DTO to generate a circular cDNA-DTO; d, the circularized cDNA-DTO is further amplified by PCR to generate a linear dsDNA with sequence tag A and tag B at its ends. In some embodiment, a single stranded DNA specific nuclease is used to digest free single stranded DTOs before self-ligation of cDNA-DTO molecule. In one embodiment, the priming sequence of the DTO comprises a random hexamer. In another embodiment, a poly(A) tail is added to the 3' end of RNA molecules by a poly(A) polymerase and a DTO with a poly(dT) is used as a primer for synthesizing a cDNA. In some embodiment, biotinylated AMPs are incorporated into the poly(A) tail of RNA molecules during the polyadenylation process. The biotin-RNA can be used to separate cDNA/biotin-RNA hybrids from unbound DTOs. In some embodiment, biotinylated dNTP can be used to incorporate biotinylated nucleotide into the cDNA during the reverse transcription reaction. The biotin-cDNA can be separated from unbound DTOs using Streptavidin magnetic beads. In some embodiment, the DTO comprises a breaking site, and the linear DNA is generated from the circular cDNA-DTO by breaking at the breaking site.

In some embodiment, the invention provides a method for making a di-tagged DNA from a single-stranded DNA sequence using a single-stranded DTO with a priming sequence. The method comprises the following steps: a, annealing the single stranded DTO to the DNA sequence; b, extending the 3' end of the DTO using a DNA polymerase to make a cDNA-DTO; c, self-ligating the 3' and 5' ends of the cDNA-DTO to form a circular cDNA-DTO. The circularized cDNA can be amplified by PCR to generate a linear dsDNA with sequence tags A and B. In one embodiment, the priming sequence of the DTO comprises a random hexamer. In another embodiment, a poly(dA) tail is added to the 3' end of the DNA molecules by a terminal transferase and a DTO with a poly(dT) is used as a primer for synthesizing a cDNA. Biotinylated dAMPs is incorporated into the poly(dA) tail of DNA molecules using a terminal transferase. The biotin-poly(dA) tail can be used to separate cDNA/biotin-DNA hybrids from unbound DTOs.

In some embodiment, the present invention provides a method of making a di-tagged single-stranded DNA from a double-stranded DNA. The method comprises the steps of the following: a, ligate a double-stranded DNA to a double-tagged oligonucleotide to generate a circular dsDNA, wherein the double-tagged oligonucleotide has a single nick or a gap; b, remove the nicked/gapped strand using exonucleases to generate a circular single-stranded DNA; c, break the circular single-stranded DNA at the breaking site to generate a linear di-tagged single-stranded DNA. In another embodiment, the double-tagged oligonucleotide comprises a stopping sequence. The DTO may or may not have a nick or gap. After the DTO and the dsDNA sequence are ligated to form a circular DNA-DTO, using one primer annealing to sequence tag A or B, single-stranded DNA can be amplified by a linear PCR. The stopping sequence ensures the generation of single-stranded DNAs with two sequence tags at the ends, preventing generation of rolling cycle products by PCR amplification.

A DTO with a stopping sequence of five abasic deoxyribonucleotides and a regular oligonucleotide of the same length were used as templates for standard PCR amplification using the same forward and backward primer pair. The DTO prohibited polymerization by DNA polymerase across the stopping sequence, resulting in very low production of PCR product. The regular oligonucleotide produced abundant PCR product of the expected size. DNA marker sizes are 25, 50, 100, 200, 300, 400, 500, 600, 700, 800, 900,1000bp.

Figure 8:
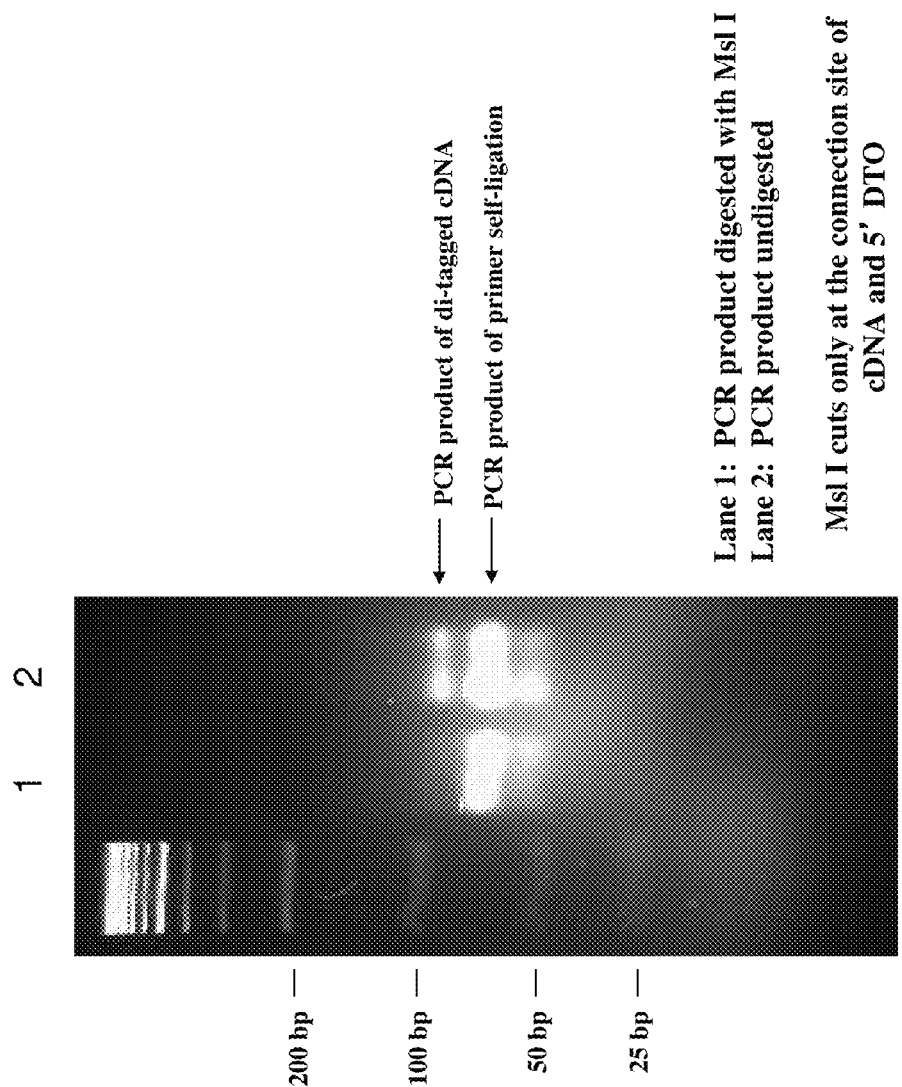

FIG. 8. Shows generation of double-tagged DNA using a DTO.

A synthesized 70 bp DTO has, from 5' to 3', a sequence A tag, five abasic deoxyribonucleotides, a sequence B tag, and a poly(dT) tail+NV. A synthesized 23 bp RNA oligo was polyadenylated using PolyA polymerase. The polyadenylated RNA oligo was purified, reverse transcribed with DTO oligo using M-MLV reverse transcrptase (Clonetech, Mountain View, Calif.) and circularized using CircLigase II (EPICENTRE, Madison, Wis.). The circularized cDNA product was amplified with 30 PCR cycles using primers corresponding to sequence tags A and B. Part of the PCR product was digested with Msl I which only cuts at the ligation junction of cDNA and 5' DTO. The size of the PCR products of DTO self-ligation and DTO-cDNA ligation are 70 bp and 93 bp, respectively. The 93 bp PCR product (upper band) disappeared after Msl I digestion, indicating that the disappearing product is the PCR product of cDNA and 5' DTA oligo ligation.

Figure 9:
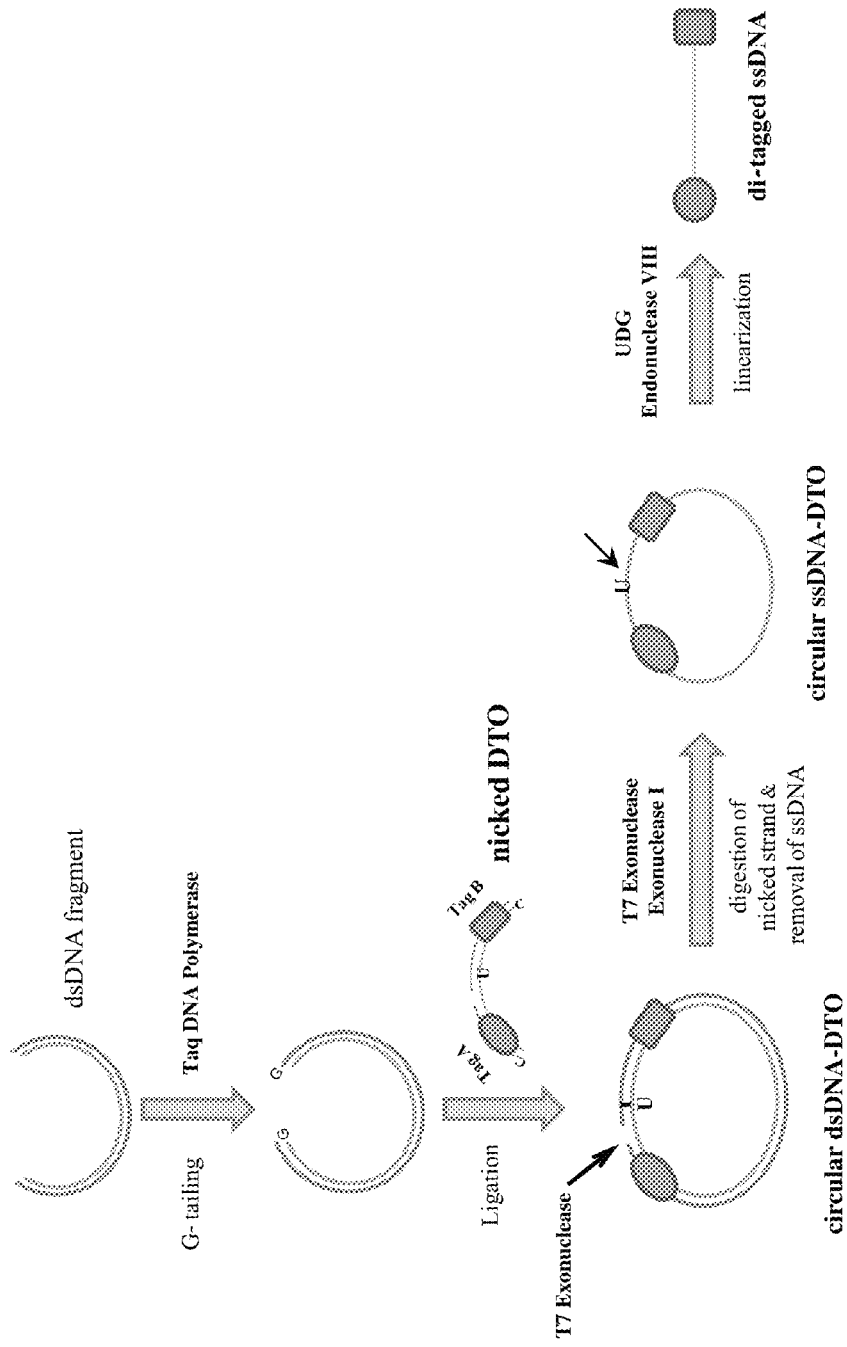

FIG. 9. A schematic illustration of making a di-tagged single stranded DNA from a dsDNA.

Figure 10:
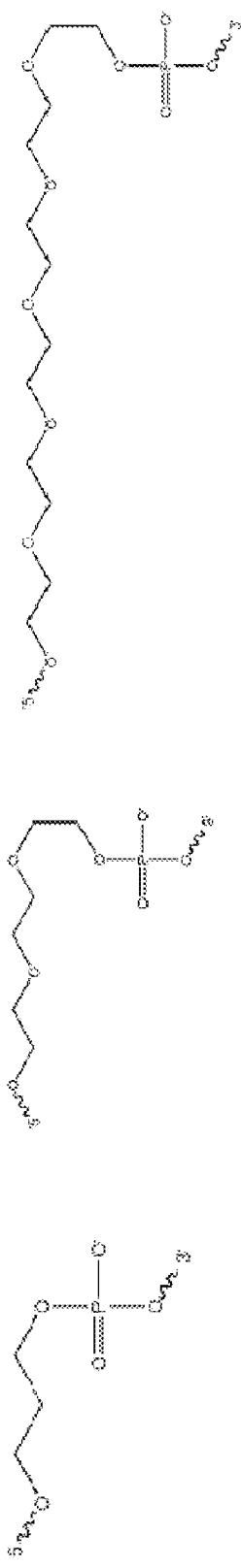
Figure 10:
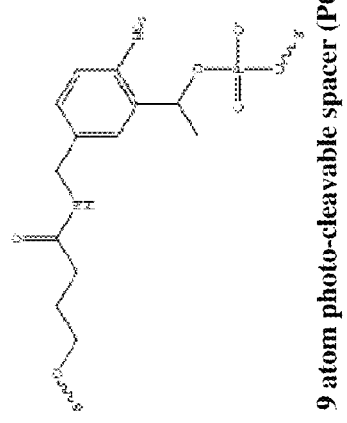

FIG. 10. Structure of nucleotide spacers

Figure 11:
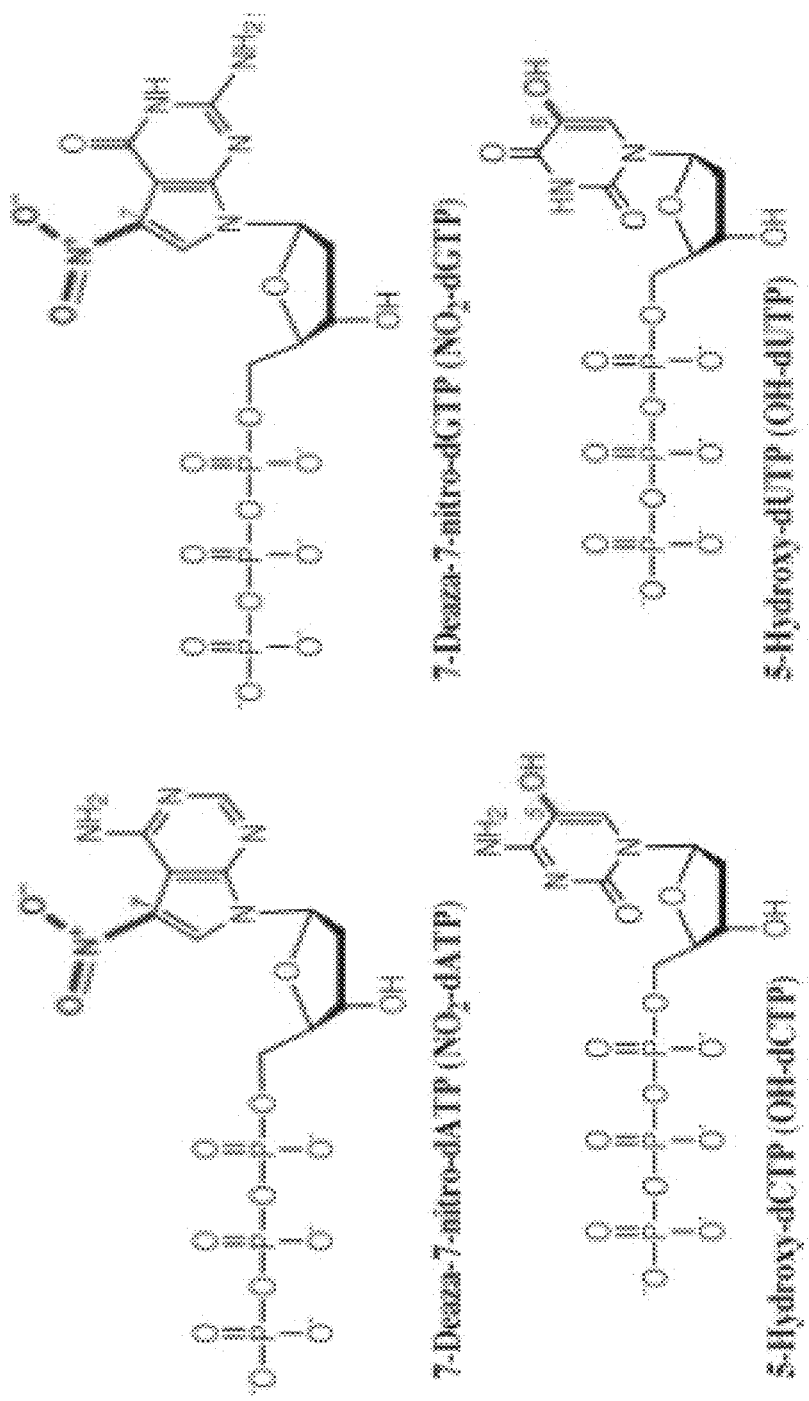

FIG. 11. Structure of nucleotide analogs

DETAILED DESCRIPTION

High-throughput sequencing technologies requires converting sequences from RNA or DNA starting materials into random small DNA fragments with different sequence tags attached at both ends. Different sequencing platforms require different sequence tags to be added to DNA fragments. The present invention employs a DTO, sequentially comprising a pre-selected sequence tag A, a linker, and a pre-selected sequence tag B. The sequence tags A and B are preselected to match sequencing platform specific sequencing tags, allowing resulting di-tagged DNAs ready to be sequenced on any sequencing platform of choice. The linker provides a breaking site or a stopping sequence.

The use of the DTO is advantageous in multiple respects. The DTO provides two pre-selected sequence tags (tag A and tag B) in a single molecule that enables highly efficient addition of two sequence tags to a cDNA via inter and intramolecular ligations. Using self-ligation for linking a sequence tag is especially effective for small inserts (e.g. siRNA and snRNA) or RNA/DNA samples with very low concentrations.

For single stranded RNA or DNA, the use of the single stranded DTOs leads to differential tagging of the 5' and the 3' ends of a cDNA sequence, which maintains the information about the strand direction of the RNA/DNA sequence of origin. For example, using a DTO (from 5' to 3', a sequence tag A, a stopping sequence, a sequence tag B, and a priming sequence) as a primer for synthesizing a cDNA, the cDNA is connected to the sequence tag B on its 5' end. The sequence tag A is connected to the 3' end of the cDNA by way of self-ligation. Using a DTO to incorporate different sequence tags into different ends of each cDNA sequence ensures that the strand of origin of the starting RNA/DNA can be ascertained.

The stopping sequence in the DTO provides an "autostop" function to prevent DNA polymerase from further extending the 3' end of a synthesizing nucleic acid. The stopping sequence comprises non-natural nucleotide analogues or other chemical moieties that function as a stop code for DNA polymerase. The stopping sequence prevents rolling circle amplification during PCR reactions, which avoids introduction of sequence bias due to differences in rolling circle efficiency. The efficiency of forming rolling circles is different for different DNA sequences depending on the size and composition of the molecules. Elimination of rolling circle amplification by the stopping sequence is advantageous by eliminating sequence bias introduced in this respect. The use of stopping sequence also provides a cleaner background. The breaking site provide a simple way to generate linear DNAs from circular DNAs.

The present invention provides a DTO having a sequence tag A, a linker, a sequence tag B. The sequence tags A and B are preselected to match sequence tags specific for sequencing platforms. The DTO can be a double stranded DNA oligo used for ligation with two ends of double stranded DNAs to form a circular molecule. The double stranded DTO may have nick(s), gap(s), modified nucleotides, abasic nucleotides, or other chemical moieties. The DTO can be a single stranded DNA oligo used as a primer for synthesizing a complementary DNA from a RNA or DNA sequence. The single stranded DTO further comprises a priming sequence at its 3' end.

The linker of a DTO comprises a natural or non-natural nucleotide sequence, or non-nucleotide chemical moieties located between sequence tags A and B. The function of the linker is to provide a breaking site or a stopping sequence. A breaking site of a DTO refers a special region of the DTO that is susceptible to photo, enzymatic or chemical cleavage. The breaking site may comprise a single-stranded DNA/RNA sequence, a double-stranded RNA, or a double-stranded DNA sequence with modified nucleotides and/or other non-nucleotide chemical moieties. In some embodiment, the breaking site comprises a single-stranded DNA sequence in a double stranded DTO that provides a cleavage site for S1 nuclease within the dsDTO. In some embodiment, the breaking site comprises uracil nucleotides, which can be converted to a baseless nucleotide by Uracil DNA Glycosylases (UDG) and be subjected to cleavage by AP endonucleases.

In some embodiment, the breaking site comprises modified nucleotides that are susceptible to chemical cleavage. For example, 5-hydroxy-dCTP, 5-hydroxy-dUTP, 7-Deaza-7-nitro-dATP, 7-Deaza-7-nitro-dGTP (see FIG. 11) are modified nucleotides that form normal base pairing and are subjected to chemical cleavage by KMnO4 and pyrrolidine treatment (Wolf, J L, Proc Natl Acad Sci USA., 2002 99(17):11073-8). A breaking site can incorporate at least one of these modified nucleotides into the each one of its strands.

In some embodiment, the breaking site comprises a photo-cleavable chemical moiety which can be cleaved by exposure to UV light. The photo-cleavable chemical moiety can be, for example, a 9 atom photo-cleavable nucleotide spacer (PC spacer, see FIG. 10) commercially available from Integrated DNA Technologies (Coralville, Iowa). The PC spacer can be incorporated into the position between sequence tag A and tag B to serve as a breaking site. Photo cleavage of a PC spacer releases an oligo nucleotide with a 5' phosphate.

The stopping sequence of the DTO comprises, instead of four natural nucleotides, chemical moieties that cannot effectively serve as templates for polymerases and function to stop enzymatic nucleic acid polymerization. Such chemical moieties include, but not limited to, modified nucleotide analogues that cannot form base pairs with natural nucleotides, modified nucleotide analogues that can form base pairs with natural nucleotides, but are structurally incompatible with polymerases, and chemical moieties with little structural similarities to nucleotides that can function to stop DNA polymerization. As the stopping sequence may comprise modified nucleotides or chemical moieties that do not form base pairing, the stopping sequence within a double stranded DTO may create a gap in the dsDTO. The 5' and 3' end nucleotides of the stopping sequence gap may be modified to confer nuclease resistance. For example, the 5' and 3' hydroxyl group can be replaced with a —NH$_2$ group so that they are resistant to nuclease cleavage.

In some embodiment, the stopping sequence comprises one or more nucleotide analogs with bases that are sterically or electronically incompatible with the active sites of polymerases, which are effective at stopping nucleic acid polymerization at the site of such analogs. For example, 4-methylidole β-nucleoside, α-naphthalene nucleoside, and α-pyrene nucleoside, which are non-polar nucleotide analogs that pairs poorly with natural nucleotide bases, can be incorporated into the DTOs as the stopping sequence. The method to synthesize and incorporate these modified nucleotide analogs into DTA oligo was described in Moran et al., Nucleic Acids Research, 1996, vol. 24, No. 11, page 2044-2052, which is incorporated by reference herein. Incorporation of one of these modified nucleotide analogs may have different efficiency as to stopping enzymatic polymerization. Incorporation of at least 2, 3, 4, 5 or more modified nucleotide analogs can greatly enhance the autostop function and lead to complete stop of nucleic acid polymerization by polymerases beyond the stopping sequence.

Figure 4:
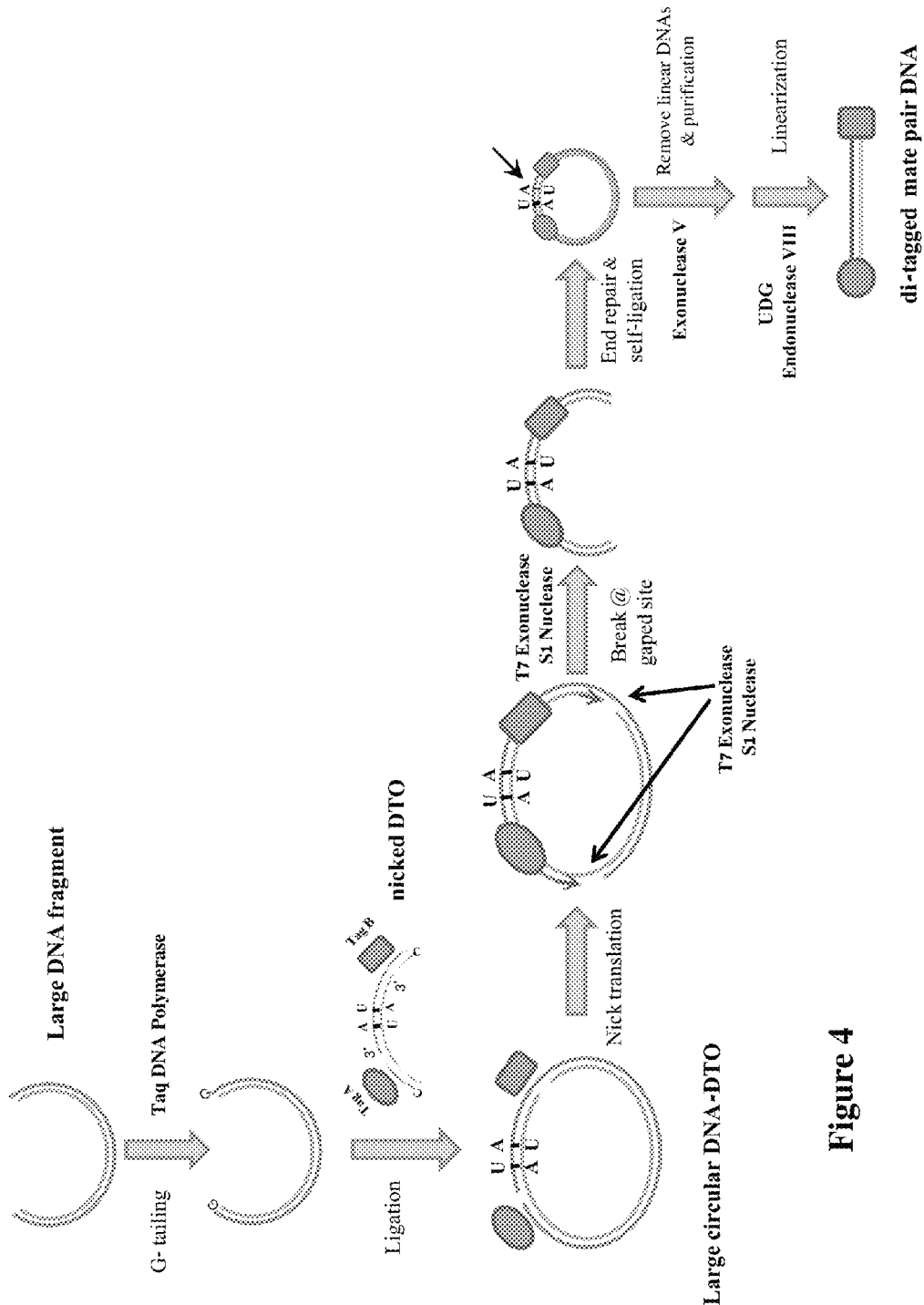
FIG. 4. A schematic illustration of making di-tagged mate pair DNAs using a nicked dsDTO.

In some embodiment, the stopping sequence comprises ribose-phosphate or deoxyribose-phosphate backbone without nucleobases. It is reported that some DNA polymerases can "read through" one abasic nucleotide and integrate a natural nucleotide on the opposite strand. Abasic nucleotides are more effective at inhibiting DNA polymerization by polymerases with 3' to 5' proofreading activities as proofreading polymerases will recognize the erroneous basepairing with abasic nucleotides and remove the erroneous nucleotide from the 3' end (Gal, et al. Analytical Biochemistry, 2000, 282, 156-158). Incorporation of more than one (e.g. 2, 3, 4, 5, or more) abasic nucleotides into the stopping sequence can effectively stall the polymerization by most polymerases. In FIG. 4, incorporation of five abasic nucleotides in a DTO effectively prevented DNA polymerase from reading through the stopping sequence.

In some embodiments, the stopping sequence comprises nucleotide analogs or mimics that can form base pairs with natural nucleotides, but cannot serve as templates for polymerases. It is contemplated that nucleotide analogs with a bulky group on its nucleobase, which may maintain the base pairing ability with natural nucleotides, but cannot fit into the active site of DNA polymerases, can also be used in the stopping sequences.

In another embodiment, the stopping sequence comprises internal spacers of different lengths between sequence tags A and B. Chemical moieties that completely lack structural similarity to natural nucleosides cannot be recognized by polymerases or used as templates for nucleic acid polymerization. When incorporated into DTOs, such chemical moieties can serve as effective stop codes for polymerases. For example, commercially available nucleotide spacers such as C3 spacer phosphoramidite, 9-atom triethylene glycol spacer, and 18-atom hexa-ethyleneglycol spacer (Integrated DNA Technologies, Coralville, Iowa) (see FIG. 10), can be incorporated into DTOs as the stopping sequence to block nucleic acid polymerization by DNA polymerases (Brukner et al. Analytical Biochemistry, 2005, 339, 345-347). In addition, multiple nucleotide spacers can be inserted between sequence tag A and B to introduce a longer spacer arm, which could more efficiently block DNA polymerization.

In some embodiment, the stopping sequence comprises a single stranded RNA or a double stranded RNA. Most DNA polymerases either cannot use RNA as template or does so at very low efficiency. Incorporating multiple ribonucleotides into a DTO sequence can effectively prevent extending DNA polymerization across the RNA region.

Further, the DTO may comprise a capture domain that allows capturing of the DTO. The term "capture domain" refers to a structure or a moiety incorporated into a nucleic acid sequence that allows the separation of the capture domain containing nucleic acid sequence and any specifically bound nucleic acids from the rest of nucleic acid populations. The capture domain may comprise an affinity binding group which allows the capture of the capture domain containing nucleic acid by affinity binding to its binding partner, or a cross-linking moiety that is capable of photochemically or chemically forming a covalent bond to other immobilized substrate. Methods to separate nucleic acids by affinity binding are well known to those of ordinary skill in the art. Non-limiting examples of the separation methods include using physical separation, ligand-receptor binding, antigen-antibody association, or complementary nucleic acid pairing. In some embodiment of the invention, a biotin moiety is incorporated into the DTO as a capture domain. The biotin-containing DTO can be separated by binding to immobilized streptavidin or avidin (e.g. streptavidin-coated magnetic beads or avidin-coated magnetic beads).

In some embodiment, the double-tagged oligonucleotide of the present invention further comprises a priming sequence. The priming sequence comprises a sequence or a mixture of sequences that is complementary to part of a RNA/DNA fragment and used as a primer for synthesizing a complementary DNA (cDNA). The priming sequence, for example, can be a mixture of random hexamers for annealing to any complementary location of a RNA/DNA sequence or a oligo(dT) for annealing to a 3' end of any RNA with a poly(A) tail.

In one embodiment, the present invention provides a method of making a di-tagged DNA library, comprising the steps of: a) providing a double-tagged oligonucleotide (DTO), sequentially comprising a sequence tag A, a linker, and a sequence tag B; b) providing a DNA or RNA fragment; c) connecting the DTO to the DNA fragment or a cDNA fragment generated from the DNA or RNA fragment to form a circular DNA-DTO molecule; d) generating a linear DNA from the circular DNA-DTO molecule with sequence tag A and tag B at its ends. The collection of such linear DNAs with sequence tag A and tag B forms a di-tagged DNA library. The DNA or RNA fragment refers to DNA or RNA sequences of certain size range generated from a DNA or RNA sample. The DNA or RNA fragment can be single stranded or double stranded. The double-stranded DNA is, under most circumstances, blunt ended DNA. A cDNA from a DNA or RNA fragment refers a DNA sequence synthesized by DNA polymerization or reverse transcription using the DNA or RNA fragment as the template. A cDNA comprises a DNA sequence complementary to its parent DNA or RNA sequence.

The DTO molecule can be a single stranded or a double stranded DNA. When a single stranded RNA fragment is provided, a single stranded DTO is used as a primer and the RNA fragment is used as a template for a reverse transcription to generate a cDNA fragment complementary to the parent RNA fragment. When a single stranded DNA fragment is provided, a single stranded DTO is used as a primer and the DNA fragment is used as a template for a DNA polymerization reaction to generate a cDNA fragment complementary to the parent DNA fragment. The DTO molecule is thus directly connected to the cDNA fragment via reverse transcription or DNA polymerization reaction. The single stranded DTO-cDNA sequence can be self-ligated to form a circular molecule. When a double stranded DNA fragment is provided, a double stranded DTO is used to ligate to two ends of the dsDNA fragment to form a circular molecule.

In some embodiment, the linear DNA fragments or free DTOs are digested by exonucleases so that they can be easily separated from the circular DNA-DTO molecules. A single exonuclease (e.g. exonuclease V) or a combination of exonucleases (e.g. Lambda exonuclease/exonuclease I) are used to digest linear DNA with free double stranded or single stranded ends. Exonuclease V has exonuclease activity towards ssDNA and dsDNA as well as endonuclease activity towards ssDNA. It can be used to remove linear ssDNA and dsDNA from closed circular dsDNAs. If circular dsDNAs have nicks or gaps, exonuclease V should not be used to remove linear DNAs due to its ssDNA endonuclease activity. Exonucleases (e.g. Lambda exonuclease) that cannot act upon nicked or gapped sites of a dsDNA should be used instead. Lambda exonuclease catalyzes removal of mononucleotides of dsDNAs from 5' to 3' direction, but cannot initiate digestion at nicks or gaps of dsDNAs. Lambda exonuclease is a good exonuclease to be used to digest linear dsDNA and free dsDTOs when a nicked or gapped circular DNA is the desired product. Lambda exonuclease digests one strand of a dsDNA, leaving a single stranded DNA, which can be digested by a single stranded DNA specific exonuclease such as exonuclease I.

There are two methods for generating a linear DNA from a circular DNA-DTO molecule. If there is a breaking site within the DTO sequence, linear DNAs with sequence tag A and tag B can be generated by breaking at the breaking site. Alternatively, using a primer pair corresponding to sequence tag A and tag B, a PCR is performed to generate a di-tagged linear DNA from the circular DNA-DTO molecule.

The linker of a DTO comprises a stopping sequence or a breaking site, wherein the stopping sequence comprises modified nucleotides or chemical moieties that can stop a DNA polymerization reaction, and the breaking site comprises a special region of the DTO that is susceptible to photo, enzymatic or chemical cleavage.

In one embodiment, the invention provides a PCR-free method for making a di-tagged DNA sequence using a double stranded DTO. The method comprises the following steps: a, ligate two ends of a dsDNA fragment to a double-stranded DTO with a breaking site to make a circular DNA-DTO; b, digest linear dsDNAs using a linear DNA specific exonuclease; c, use an appropriate method to cleave the circular DNA-DTO sequence at the breaking site to generate a linear DNA sequence with two different sequence tags at each end of the sequence. Conventional method for adding two sequence tags to DNA fragments involves randomly ligating two sequence tags to DNA fragments. This method results in ligation products with only one sequence tag, two of the same sequence tag, and two different sequence tags. A PCR is needed to selectively amplify the ligation products with two sequence tags. The present invention directly connects the two ends of a DNA to two different sequence tags in a DTO molecule. The advantage of this method is that no PCR amplification is required, therefore eliminating possible sequence bias caused by PCR.

For this method to be effective, it is very important to minimize self-ligation within DTOs or DNA fragments, and increase the efficiency of 1:1 (DTO: DNA fragment) ligation. In some embodiment, a single Adenine nucleotide is added to the 3' end of the dsDNA fragment using a non-proofreading polymerase (e.g. Taq DNA polymerase or Klenow fragments, 3'-5' exo minus). A single 3' T-overhang is added to the double-stranded DTO to minimize self-ligation. When ligating A-tailing DNA fragments and T-overhang DTOs, self-ligation within DNA fragments or DTOs can be minimized. Although using A/T tailing in DNA ligation is quite common in practice, ligation of DNAs with G/C tailing gives much higher ligation efficiency. A single Guanine nucleotide can be added to a blunt ended dsDNA using a non-proofreading polymerase such as Taq DNA polymerase. Incubating a blunt ended dsDNA with Taq DNA polymerase in the presence dGTP only adds one single GMP to 3' end of the dsDNA. The addition of dGMP to the end of dsDNAs is as efficient as addition of dAMP by DNA polymerases (U.S. Pat. No. 7,723, 103). DTOs with a single C-overhang are then used to ligate with the DNAs with a single G-tailing. Nucleotide tailing can also be added to the 3' end of DNA fragments using terminal deoxynucleotidyltransferases (Promega, Madison, Wis.). Terminal deoxynucleotidyltransferases adds one or more template-independent nucleotides to the 3' terminal of DNA fragments, and complementary nucleotide overhangs should be added to DTOs. Since the number of nucleotides added by terminal deoxynucleotidyltransferases to a DNA molecule is not fixed, during the ligation, a DNA ligase is added together with a DNA polymerase that can extend 3' end to fill gaps between the ends of DTOs and DNA fragments. Using G/C pair overhang can greatly increase ligation efficiency between DTO and DNA fragments while minimizing self-ligation within DTOs and DNA fragments themselves. The ratio between DTO and DNA fragments in the ligation reaction can be varied to favor 1:1 (DTO:DNA fragment) ligation. This ratio (DTO:DNA fragment) can vary from 2:1, 3:1, 4:1, 5:1, 6:1, 7:1, 8:1, 9:1, to 10:1, or higher.

After the ligation, an exonuclease (e.g. Exonuclease V (NEB) or Plasmid-Safe™ DNase (Illumina)) or a combination of exonuclease (e.g. T7 exonuclease/exonuclease I or Lambda exonuclease/exonuclease combination) that catalyzes hydrolysis of linear DNAs is added to remove linear DNAs including unligated DTOs, unligated DNA fragments, and linear ligation products. The digested products including mononucleotides and small oligonucleotides, and exonuclease enzyme are removed from circular DNA-DTOs by DNA purification methods known to those skilled in the art. In another embodiment, a biotin moiety can be incorporated into DTOs and ligated DTO-DNA products can be separated from unligated DNA fragments using streptavidin beads.

The breaking site of the DTO may comprise, for example, a single-stranded DNA/RNA, Uracil nucleotides, or other chemical moieties, which allows photo cleavage, enzymatic cleavage or chemical cleavage at the breaking site. In some embodiment, DTOs have a single-stranded DNA or RNA sequence as the breaking site. A circular dsDNA-DTO is formed with a stretch of single-stranded sequence between sequence tags A and B. S1 nuclease, an endonuclease active against single-stranded DNA or RNA sequences, can be used to cleave the singe-stranded region of the circular DNA and generate a linear DNA sequence with tags A and B. In another embodiment, the breaking site is incorporated with uracil nucleotides on both strands. Uracil DNA Glycosylase (UDG) is used to remove a uracil base from the uracil nucleotide to form an abasic site (apurinic/apyramidinic site, also called AP site) while leaving the sugar-phosphate backbone intact. AP endonuclease (e.g. endonuclease VIII) is then used to cleave DNA at the AP site and create a one nucleotide gap at the site of uracil nucleotide. When a uracil is incorporated in both strands of the breaking site in a double-stranded DTO, the combined treatment of UDG enzyme and AP endonuclease releases a linear DNA with sequence tags A and B at its ends. In another embodiment, a photo-cleavable nucleotide spacer is incorporated between sequence tag A and tag B. A linear DNA is generated from the circular DNA-DTO molecular by cleaving the photo-cleavable spacer from the circular molecule upon UV exposure. In another embodiment, nucleotide analogs susceptible to chemical cleavage is incorporated into the breaking site. For example, at least one of the nucleotide analogs selected from 5-hydroxy-dCTP, 5-hydroxy-dUTP, 7-Deaza-7-nitro-dATP, or 7-Deaza-7-nitro-dGTP can be incorporated in each strand of the dsDTO molecule. Chemical treatment of $KMnO_4$ and pyrrolidine cleaves the nucleotide analogs from the circular DNA-DTO molecule, generating a linear dsDNA with sequence tag A and tag B.

In some embodiment, PCR amplification is needed to increase the amount of di-tagged dsDNA output. The invention provides a method of making a di-tagged DNA comprises the steps of the following: a, ligate a double-stranded DTO to DNA fragments to form a circular DNA-DTO product; b, use sequence tag A and B as PCR primers to amplify the DNA fragments with sequence tag A and B at both ends. In this method, it is desirable to have a stopping sequence to get a cleaner PCR product and prevent formation of rolling cycle products. A stopping sequence, however, is not required in this method. The DTO may comprise sequence tag A and B without a linker sequence in between.

Mate pair DNA refers to a DNA sequence comprising two DNA segments originally located long distance apart, usually more than several kilobases, in the genome. A mate pair library is comprised of mate pair DNA sequences with two different sequence tags attached at the ends. In one embodiment, the present invention provides a simple and highly efficient method for making mate pair DNA libraries. The method comprises the following steps: a, ligate a DTO to two ends of large DNA fragments to generate large circular DNAs; b, randomly fragment large circular DNAs to small DNA fragments; c, perform end repair of the small DNA fragments to make ready for ligation; d, self-ligate the small DNA fragments to generate small circular DNA; e, perform PCR with the small circular DNA to generate a linear DNA with tags A and B, which contains sequences of both ends from a same large DNA fragment.

Ligation of a DTO to two ends of a large DNA fragment results in a circular DNA where both ends of the large DNA fragment are linked to sequence tags A and B in the DTO. In some embodiment, exonucleases are added to remove linear dsDNA including unligated dsDTOs, linear DNA fragments and linear ligation products. Exonucleases that specifically digest linear double stranded DNA, but have very little activity towards closed circle dsDNA can be used herein. Examples of such exonucleases include exonuclease V and Plasmid-Safe™ DNase (an ATP-dependent DNase available from Illumina (San Diego, Calif.) that digests linear dsDNA, but not nicked or closed-circle dsDNA). The large circular DNAs are then purified from exonuclease enzymes and the digestion products using DNA purification and extraction kits from commercial sources such as Qiagen (Valencia, Calif.), Agilent Technology (Santa Clara, Calif.), and Beckman Coulter (Brea, Calif.). The large circular DNAs are randomly fragmented to smaller DNA fragments using methods well known to person skilled in the art, including physical (e.g. sonication, physical shearing, and nebulization) and enzymatic means (e.g. use of DNAse I or Benzonase). The small DNA fragments then undergo an end repair process, and are converted to be blunt ended with 5'-phosphate and 3'-OH, which is ready for blunt end ligation. The end repair kits are available from multiple commercial sources such as NEB, Invitrogen, and Illumina. After self-ligation of the small DNA fragments, those containing sequence tags A and B are amplified by PCR reactions using primers corresponding to sequence tags A and B.

In some embodiment, exonucleases (e.g. exonuclease V or Plasmid-Safe™ DNase) are added to digest linear unligated dsDNA. The small circular DNAs are then purified using DNA purification and extraction kits before proceeding to PCR amplification. In some embodiment, the DTO comprises a breaking site, and the small circular DNA is cleaved at the breaking site to generate a linear DNA. PCR amplification is performed against the linear DNA to select DNA with two sequence tags. In some embodiment, the DTO comprises a stopping sequence, and PCR amplification is performed directly on small circular DNAs to generate linear di-tagged DNAs. In another embodiment, modified nucleotide (e.g. biotinylated nucleotide) can be incorporated into DTO sequences. large and small circular DNA containing biotinylated DTO sequences can be isolated and enriched using streptavidin beads. Biotin-nucleotide can be incorporated in the middle of DTO sequences, not at the ends. This helps to alleviate the problem of low ligation efficiency caused by end biotin-nucleotides.

In some embodiment, the present invention provides a method of making a mate pair DNA libraries from large DNA fragments using a nicked DTO. The method comprises the steps of the following: a, ligate both ends of a large DNA fragments to a double-tagged oligonucleotide to generate a large circular DNA, wherein the double-tagged oligonucleotide has a nick site on each of the opposite strand; b, perform a nick translation to elongate the 3' end of each nick site; c, break the large circular DNA at the nick sites to generate a smaller linear DNA with the double-tagged oligonucleotide; d, end repair the small linear DNA to make it ligation ready; e. self-ligate the small linear DNA to form a small circular DNA that contains end sequences of a large DNA fragment and double-tagged oligonucleotide; f, perform PCR to amplify mate pair sequences between sequence tags A and B.

A nick in a dsDNA refers to a break of a phosphodiester bond of adjacent nucleotides in one strand. The nick sites can be introduced at any location along the DTO sequence, but not at the same location. Preferably, the nick site is positioned relatively close to the 3' end of the DTO strand and both nicks are positioned about the same distance away from the 3' termini. For example, the nick sites can be positioned 6, 7, 8, 9, 10, 11, 12, 13, 14, 15, 16, or more nucleotides away from the 3' end. Nick sites can be sealed by DNA ligase if both 5' phosphate and 3' hydroxyl group are available. To prevent nick sites from being sealed during ligation, the 5' phosphate group of both nick sites is replaced with a 5' hydroxyl group. To increase ligation efficiency between DTO molecules and large DNA fragments, a C or T-overhang is added to the 3' end of DTO molecules, and a complementary G or A-tailing is added to the blunt end of large DNA fragments using a non-proofreading DNA polymerase (e.g. Taq DNA ploymerase or Klenow fragment (exo-)).

After ligation, a nick translation is performed to extend the 3' end of the nicks. A nick translation is elongating nucleotides from 3' end of a nick by a DNA polymerase, and at the same time removing nucleotides from 5'->3' and replacing an old strand with a newly formed strand. DNA polymerases (e.g. *E. coli* DNA polymerase I) that have both DNA polymerase activity and 5'->3' exonuclease activity can be used for nick translation. The elongation distance is dependent on the processivity of the DNA polymerase used. By varying the amount of enzyme activity, incubation time and temperature, the number of bases added by a nick translation can be controlled. Preferably, the number of elongated bases from each nicked site is within the range of 50 bp to 300 bp so that the resulting di-tagged DNA is about 100 bp to 600 bp in length. The di-tagged DNA thus has about 50 bp to 300 bp sequences from each end of the parent DNA fragment. After nick translation, add an exonuclease with 5'->3' activity (e.g. T7 exonuclease) to partially digest away the nicked strand and create a single-stranded gap region, which is subjected to cleavage by single-stranded DNA/RNA specific nuclease such as S1 nuclease. Quickly inactivate exonuclease after digestion is complete, and use DNA purification methods (e.g. phenol chloroform extraction, or Agencourt AmPure DNA purification kit) to completely remove the exonuclease. Residual nuclease activity could lead to degradation of final products. After the exonuclease is inactivated and removed, S1 nuclease is added to make a cleavage at the single-stranded region to release a smaller linear DNA fragment, namely a small linear DNA-DTO fragment, which contains two end sequences of an original large DNA fragment linked by a DTO sequence. The small linear DNA fragments are end repaired to become blunt ended DNA. The blunt ended DNAs are incubated with T4 DNA ligase to form small circular DNAs. The unligated linear dsDNAs are removed by exonuclease treatment. PCR amplification is performed on the small circular DNAs to select dsDNAs with sequence tag A and tag B at the ends.

In some embodiment, biotin-nucleotide can be incorporated into DTO sequences and biotinylated DNA-DTO fragments can be enriched by binding to streptavidin-coated magnetic beads. The end repair and self-ligation can be performed on the small linear DNA-DTO fragments bound to streptavidin beads. Self-ligation of linear DNA-DTO sequence produces a small circular DTO-DNA sequence that two end sequences of an original large DNA fragment are linked together with a DTO sequence. Using PCR primers corresponding to sequence tags A and B, the small circular DNA-DTO products can be amplified by PCR to generate linear di-tagged mate pair DNAs. In some embodiment, the linker of DTO molecules comprises a stopping sequence, which can lead to cleaner PCR amplification products. In some embodiment, the linker region of DTO molecules comprises a breaking site, which provides a site for breaking the small circular DNA-DTO molecule to generate a linear mate pair DNA with sequence tags A and B at its ends. This linear mate pair DNA can be further amplified by PCR.

In one embodiment, the invention provides a method for making a di-tagged dsDNA sequence from a RNA sequence. The method comprises the following steps: a, annealing a DTO to the RNA sequence, wherein the DTO has, from 5' to 3', a sequence tag A, a stopping sequence, a sequence tag B, and a priming sequence; b, performing a reverse transcription to extend the 3' end of the DTO to make a cDNA-DTO molecule; c, self-ligating the 3' and 5' ends of the cDNA-DTO to generate a circular cDNA-DTO. The circularized cDNA-DTO is amplified by PCR to generate a linear dsDNA with sequence tag A and tag B. This method can be used for converting a variety of RNAs such as total RNAs, mRNAs, rRNA depleted RNAs, and small RNAs into di-tagged dsDNAs.

In some embodiment of the present invention, the DTO comprises a mixture of oligonucleotides with the priming sequence of each oligonucleotide having a random sequence, for example, a random hexamer. Random hexamers can be primed to any complementary locations on a RNA sequence. When using unfragmented RNAs as templates, the ratio of DTOs and RNA templates can be adjusted to favor production of small cDNA sequences. For example, using 250 ng hexamer primers per 5 µg of RNA can increase yield of small cDNA products (<500 bp). To further favor generation of small cDNA fragments, reverse transcriptases with less progressive activities could be chosen for the reverse transcription. An important advantage of this method is that it allows generation of small cDNA fragments from RNA molecules without fragmentation. Alternatively, RNA samples can be first fragmented into desired sizes using methods that are known to the people skilled in the art. For example, RNA can be fragmented by heat or chemical treatments as described by Cloonan et al. (Nature Methods, 2008, 5: 613-619). The DTOs with random hexamers can then be used to anneal to fragmented RNA templates and be extended by reverse transcriptases to make cDNAs. The 3' and 5' ends of a single stranded cDNA-DTO are ligated using a ligase that can ligate single stranded DNAs. T4 RNA ligase or CircLigase™ ssDNA ligase (Illumina, San Diego, Calif.) can ligate single stranded DNA and can be used for this purpose. CircLigase™ ssDNA ligase is a ligase that catalyzes intramolecular ligation (i.e. circularization) of ssDNA templates having a 5'-phosphate and a 3'-hydroxyl group. The efficiency of self-ligation depends on the length of cDNA sequences. The self-ligation based method should be most effective for converting small/micro RNAs to di-tagged small DNAs. This self-ligation based method also has advantages in working with very small amount of start materials as the self-ligation efficiency is less affected by low concentrations of RNA/DNA molecules.

In some embodiments, a polyadenine (poly(A)) tail is added to a RNA fragment using a polynucleotide adenylyltransferase, also named poly(A) polymerase, and a poly(dT) tail is used as the priming sequence in the DTO. To anchor the DTO to the junction of poly(A) tail and non-poly(A) region of the RNA molecule, a joining sequence is added adjacent to the 3' end of the poly(dT) tail. The joining sequence has a general formula of 5'-$MN_1MN_2 \ldots N_x$-3' wherein M is any natural deoxyribonucleotide other than thymine nucleotide, N is any of four natural nucleotides, dAMP, dTMP, dCMP, dGMP, and x is an integer from 1 to 10, preferably 1 to 3.

When this method is applied to make library preparations from fragmented RNAs, addition of a poly(A) tail to fragmented RNAs provides a priming site and ensures that cDNA synthesis starts from the 3'end of RNA fragments. For quantifying the amount of mRNA species using high throughput sequencing, directly measuring the amount of RNA species with a poly(A) tail is sufficient. The DTOs with a poly(T) tail can be directly used to prime cDNA synthesis of poly(A)-RNAs. Addition of a polynucleotide other than a poly(A) tail to 3' of RNA molecules can also serve the purpose of adding a priming site on RNA molecules. For example, a poly(U) polymerase (NEB, Ipswich, Mass.) can be used to add a poly(U) tail to RNAs. A person skilled in the art will understand that the present method of the invention can be similarly applied to RNAs with polynucleotide tails other than poly(A) tails.

Self-ligation of DTOs during the ligation step is an undesirable side effect that could become especially problematic when the amount of starting materials is very low. In some embodiment, a single stranded nucleic acid specific nuclease is used to digest the un-annealed single stranded DTOs. For example, exonuclease I, exonuclease T or Mung Bean nuclease can be used for this purpose. In another embodiment of the invention, a capture domain is added to RNA molecules and is used to separate DTOs annealed to RNA molecules from the un-annealed ones. A capture domain refers to a chemical structure or moiety incorporated into a nucleic acid sequence that allows the separation of the capture domain containing nucleic acid sequence and any specifically bound nucleic acids from the rest of nucleic acid populations. For example, a biotin-ATP can be incorporated into RNA molecules using poly(A) polymerase and biotin-RNAs and the associated DTOs or cDNAs can be captured by streptavidin or avidin-coated magnetic beads. The unbound DTOs can be washed away before ligation reaction. Biotin-ATP can be incorporated efficiently by the Poly (A) Polymerase. The tailing length and biotin density can be controlled by optimizing the reaction time, the ATP/biotin-ATP ratio and the total ATP concentration. In some embodiment, a ATP/biotin-ATP mixture is added during a polyadenylation reaction and biotin-AMPs are randomly incorporated into poly(A) tails. To ensure that biotin-AMPs are not incorporated adjacent to the 3' end of RNA sequences, biotin-ATPs can be added at a later time of the polyadenylation reaction. A biotin-(3'-deoxy)ATP can be added at the end of a polyadenylation reaction to add only one terminal biotin-(3'-deoxy)AMP to poly(A) tails. Alternatively, biotinylated dNTP can be incorporated into the cDNA during the reverse transcription reaction. Some Reverse transcriptase (e.g. M-MLV reverse transcriptase) can efficiently incorporate biotinylated dNTP into cDNA sequences. The procedure to incorporate biotinylated dNTP into cDNA sequences is well known to those skilled in the art and is well described in technical publications, for example, technical articles from Trilink Biotechnologies (San Diego, Calif.). The biotin-cDNA can then be separated from unbound DTOs using Streptavidin coated magnetic beads.

The invention provides a method for making a di-tagged dsDNA from a single stranded DNA sequence using a single stranded DTO, wherein the DTO has, from 5' to 3', a sequence tag A, a stopping sequence, a sequence tag B, and a priming sequence. The method comprises the following steps: a, annealing the ssDTO to the ssDNA sequence; b, extending the 3' end of the DTO using a DNA polymerase to make a cDNA-DTO; c, ligating the 3' and 5' ends of the cDNA-DTO to form a circular cDNA-DTO molecule. The circularized cDNA-DTO can be amplified by PCR to generate a linear dsDNA with sequence tags A and B. In one embodiment, the priming sequence of the DTO comprises a random hexamer. In another embodiment, a poly(dA) tail is added to the 3' end of DNA molecules by a terminal transferase and a DTO with a poly(dT) is used as a primer for synthesizing a cDNA. Biotinylated dAMPs is incorporated into the poly(dA) tail of DNA molecules using a terminal transferase. The biotin-poly (dA) tail can be used to separate cDNA/biotin-DNA hybrids from unbound DTOs. In another embodiment, a single stranded nucleic acid specific nuclease (e.g. exonuclease I, exonuclease T, or Mung Bean nuclease) is used to digest single stranded DTO molecules.

Preparation of single-stranded DNA is useful in many applications, such as DNA methylation assays or used as capturing probes. The present invention provides a method of making a di-tagged single-stranded DNA from a double-stranded DNA. The method comprises the steps of the following: a, ligate a double-stranded DNA to a double-tagged oligonucleotide to generate a circular dsDNA, wherein the double-tagged oligonucleotide sequentially comprises a sequence tag A, a breaking site, a sequence tag B, and wherein the double-tagged oligonucleotide has a nick or a gap; b, remove the nicked/gapped strand using an exonuclease to generate a circular single-stranded DNA; c, break the circular single-stranded DNA at the breaking site to generate a linear di-tagged single-stranded DNA.

A double-stranded DTO with at least one single nick or a gap in one of the two strands is used in this method. The 5' end of the nick is a hydroxyl group so that it cannot be sealed during ligation. The double-tagged oligonucleotide has either a blunt end or a C- or T overhang. The breaking site of the DTO comprises a Uracil-nucleotide on the un-nicked/un-gapped strand. Ligate a DTO sequence with one nick/gap to a dsDNA to generate a circular dsDNA with a nick or a gap. To remove the nicked or gapped strand of the circular dsDNA, incubate the circular dsDNA with an exonuclease that is able to progressively cleave nucleotides from a nick site or a gap of a dsDNA. Examples of such exonucleases include T7 exonuclease, which can initiate a progressive cleavage from 5'->3', and exonuclease III, which can remove nucleotides from 3'->5'. After digestion is complete, quickly inactivate exonucleases and use DNA purification and extraction methods (e.g. phenol chloroform extraction, cesium chloride centrifugation or Agencourt AmPure beads-based DNA purification methods) to remove exonucleases from the single-stranded circular DNA. Residual enzyme activity could lead to degradation of desired DNA products. After the exonuclease is removed, the circular ssDNA can be cleaved at the breaking site of Uracil-nucleotide when incubating with UDG enzyme and an AP endonuclease such as endonuclease VIII, therefore generating a linear single-stranded DNA with sequence tag A and B at its ends. In some embodiment, the breaking site of the DTO comprises a single stranded RNA, which can be cleaved by RNase treatment.

In another embodiment, the double-tagged oligonucleotide comprises a stopping sequence. Since nucleotide analogs or other non-nucleotide chemical moieties constituted of stopping sequence cannot form normal base pairing under most circumstances, a stopping sequence in a double stranded DTO is likely to create a unconnected gap. For example, one strand of the double stranded DTO may comprise a stretch of abasic nucleotides linking sequence tag A and tag B, and the other strand comprises a sequence tag A and tag B unconnected. In some embodiment, the stopping sequence comprises a single stranded RNA or a double stranded RNA. Most DNA polymerases either cannot use RNA as template or does so at very low efficiency. Incorporating multiple ribonucleotides into a DTO sequence can effectively prevent extending DNA polymerization across the RNA region. After the DTO and the dsDNA sequence are ligated to form a circular DNA-DTO, using one primer annealing to either sequence tag A or B, single-stranded DNA can be amplified by a linear PCR. The stopping sequence ensures the generation of single-stranded DNAs with two sequence tags at the ends and prevents formation of rolling cycle products by PCR amplification.

EXAMPLES

Example 1

A PCR-free Method for Making a Di-tagged DNA Library

Figure 1:
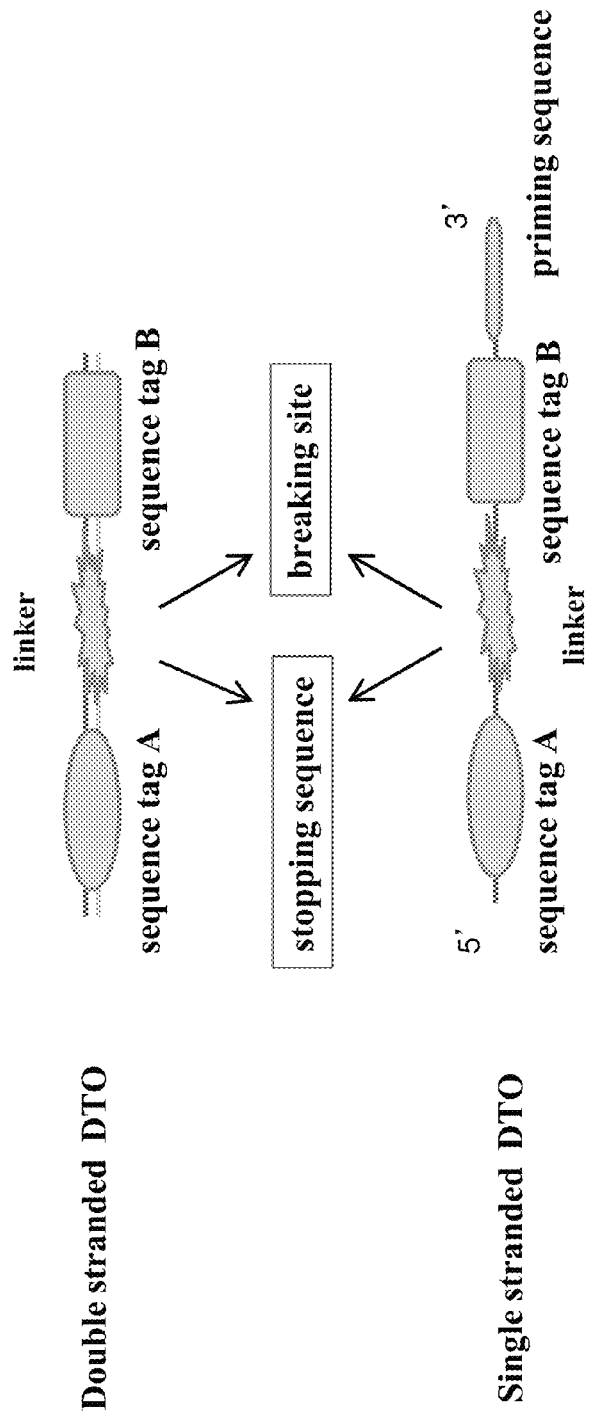
FIG. 1. A scheme of double-tagged oligonucleotides.
Figure 2:
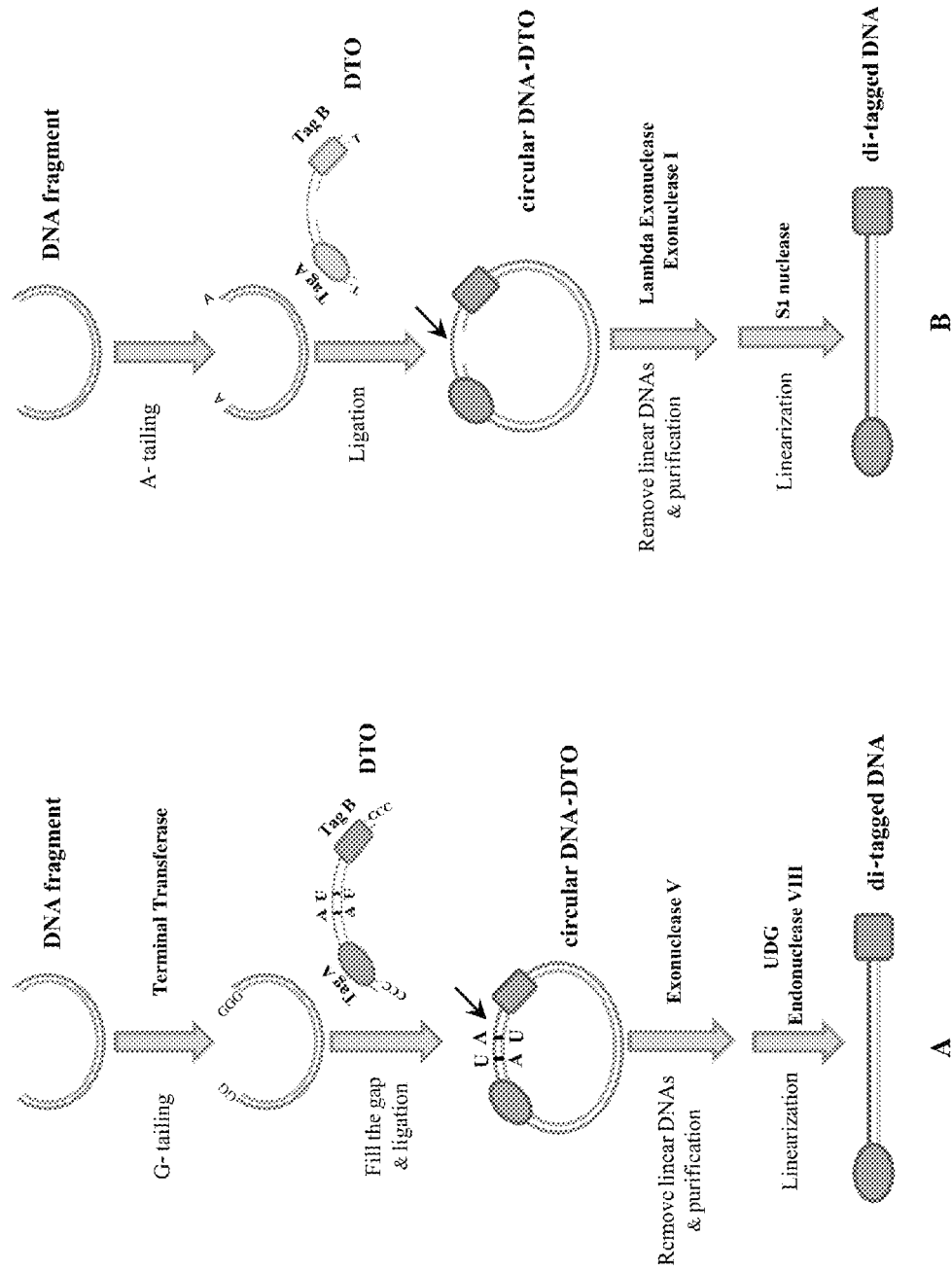
FIG. 2. A schematic illustration of a PCR-free method for adding two tags to a dsDNA using a DTO. 2A, method for making di-tagged DNAs using a DTO with uracil nucleotides. 2B, method for making di-tagged DNAs using a DTO with a single stranded gap.

Conventional methods randomly ligating two sequence tags to DNA fragments result in ligation products with only one tag, two of the same tag, and two different tags at ends of the DNA sequences. A PCR is needed to selectively amplify the ligation products with two sequence tags. This example (FIG. 2A) shows how to make di-tagged DNA libraries from DNA fragments using a double-tagged oligonucleotide. This method does not need PCR amplification or selection. The starting material is blunt ended DNA fragments. A DTO sequence having a sequence tag A, a breaking site, and a sequence B is used in this example. The breaking site of the DTO sequence has at least one Uracil nucleotide in each of two strands.

G-Tailing of DNA Fragments

Ligation efficiency between blunt end or A/T pair nucleotides is usually quite low. In order to increase ligation efficiency, Guanine nucleotides are added to 3' OH terminus of DNA fragments using terminal deoxynucleotidyltransferase. Terminal deoxynucleotidyltransferase is a template-independent DNA polymerase that catalyzes repetitive addition of deoxyribonucleotides to 3' OH of a DNA molecule. Incubate blunt ended DNA fragments with a terminal deoxynucleotidyl transferase (Illumina, San Diego, Calif.) and dGTP to add Guanine nucleotides to the 3' end of DNA fragments. By varying enzyme concentration, incubation time, and dGTP to DNA fragment ratio, the reaction can be controlled so that one to five Guanine nucleotides are added to the termini of DNA fragments. To be complementary to the 3' G overhang of DNA fragments, A stretch of five Cytosine nucleotides 3' overhang is added to the DTO sequence.

DNA Ligation and Circularization

Incubate DNA fragments with 3' G overhang, DTOs with 3' C overhang, T4 DNA ligase, and a DNA polymerase I, large fragment (exo-), which maintains 5'->3' DNA polymerase activity, but lacks 3'->5' and 5'->3' exonuclease activity in the presence of dGTP and dCTP. 3' C overhang of DTO sequences anneals to 3' G overhang of DNA fragments. The DNA polymerase I, large fragment (exo-) adds G or C nucleotides to fill in any gap between the annealing strands. T4 DNA ligase further ligates two strands to form a circular product where both ends of DNA fragments are linked to sequence tags A and B of DTO molecule. Incubate the ligation reaction mixture with exonuclease V which catalyzes digestion of unligated DNA fragments, unligated DTOs, and linear ligation products. The circular DNA-DTO ligation products are purified with AMPure XP beads (Beckman Coulter, Brea, Calif.) to remove free dNTP, free DTO and enzymes.

Generation of Linear DNA Library

The purified circular DNA-DTO product is linearized by incubating with Uracil DNA Glycosylase (UDG) and endonuclease VIII according to the protocol of NEB (Ispwich, Mass.). The combination of UDG and endonuclease VIII generates a break at the position of Uracil nucleotide and releases a linear DNA with sequence tags A and B at its ends.

Example 2

Method for Making a Di-tagged DNA Library Using a Gapped DTO

This example illustrates a method of making di-tagged DNA library from dsDNA fragments using a gapped dsDTO. The DTO has a sequence tag A, a single stranded gap (as a breaking site), sequence tag B, and a 3' dT overhang (see FIG. 2B).

A-tailing of DNA Fragments and Ligation of DNA Fragments & DTOs

The blunt ended DNA fragments are incubated with Taq DNA polymerase in the presence of only dATP and a single dA is added to the 3' terminus of DNA fragments. DNA fragments with an A-overhang are ligated to DTO with a dT-overhang to form a circular DNA-DTO molecule. The circular DNA-DTO molecule has a single stranded gap with free 3' and 5' termini on the gapped strand. Lambda exonuclease that catalyzes removal of nucleotides from 5' to 3', but cannot act on nicks or gaps of a dsDNA, is used to remove unligated dsDNA, free dsDTO, and linear ligation products while leaving the circular ligation products intact. Exonuclease I is used to further digest the single stranded DNA resulted from Lambda exonuclease digestion. After digestion, exonucleases are denatured and removed by phenol chloroform extraction and ethanol precipitation.

Generation of Linear Di-tagged DNA

The purified circular DNA-DTOs are treated with S1 nuclease to generate linear di-tagged DNAs. If needed, further PCR amplification can be performed to amplify the di-tagged DNA.

Example 3

Method for Making a Mate Pair DNA Library Using a Double-stranded DTO

Figure 3:
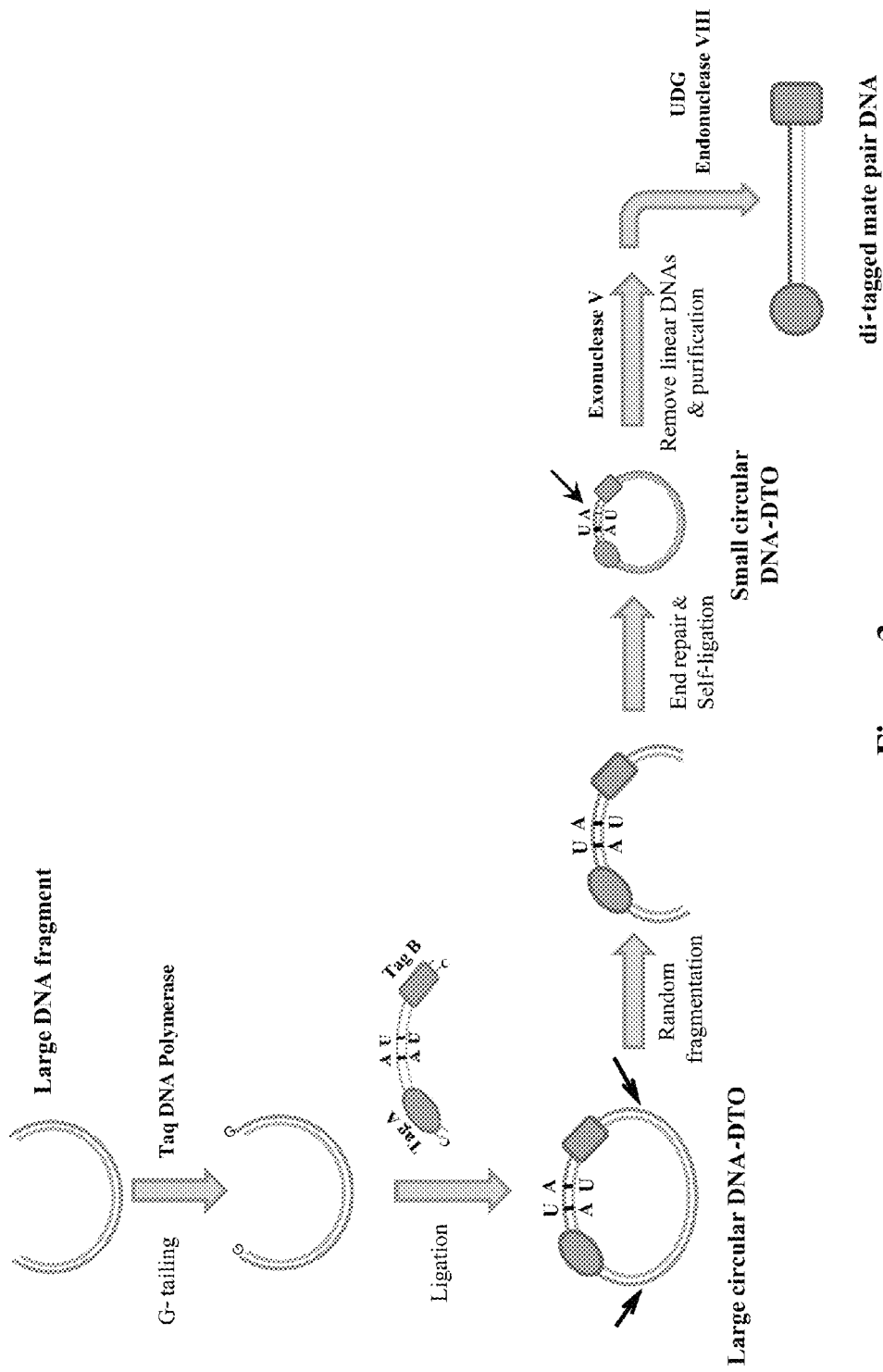
FIG. 3. A schematic illustration of making di-tagged mate pair DNAs using a dsDTO.

This example shows a method of using a double-stranded DTO to make a di-tagged mate pair DNA library containing two DNA segments that are separated by several kilobases in the genome (FIG. 3). A DTO sequence having a sequence tag A, a uracil nucleotide on each of its two strand (as a breaking site), and a sequence tag B is used in this method. A 3' dC overhang is added to the DTO sequences.

Ligation of DTO and Large DNA Fragments

Genomic DNA is fragmented into large DNA fragments of 2-3 kb in size, and is end-repaired to generate blunted end fragments having 5' phosphate and 3' OH. The large DNA fragments are incubated with Taq DNA polymerase in the presence of dGTP only. Taq DNA polymerase adds one single 3' GMP overhang to blunt ended dsDNAs. The two ends of large DNA fragment with a single dG tail are ligated to a DTO with a dC overhang to form a large circular DNA-DTO molecule using T4 DNA ligases. The unligated linear DNA sequences, unligated DTOs, and linear ligation products are digested by exonuclease V. The large circular DNA-DTO molecules are purified using AMPure XP beads, with enzymes, short oligonucleotides, and mononucleotides being removed.

Random Fragmentation to Self-ligation to Generate Circular Mate Pair DNA

The large circular DNA-DTO molecules are randomly fragmented into smaller fragments, for example, 200 to 400 bp in size, using nebulization. The small DNA fragments are end repaired to generate blunt ended DNA using NEB End repair module. After end repair, the small DNA fragments are incubated with T4 DNA ligase to form self-ligation products. The circular self-ligation DNA with DTO sequences comprises mate pair DNAs having sequences from both ends of the original large DNA fragments. The linear DNAs are removed by exonuclease V treatment and small circular DNAs are purified using AMPure XP beads.

PCR Amplification to Generate Linear Mate Pair DNA

Treat the small circular DNAs with UDG and endonuclease VIII to generate a linear DNA with sequence tag A and tag B. Perform 5 to 15 cycles of PCR to amplify DNAs between sequence tag A and tag B. If needed, size selection and purification of linear mate pair DNAs can be performed on an agarose gel.

Example 4

Method for Making a Mate Pair DNA Library Using a Nicked dsDTO

This example shows a method of using a nicked DTO to make a di-tagged mate pair DNA library (FIG. 3). The nicked DTO sequence used in this example has a nick in each of the two strands, wherein the nick has a 5' and 3' hydroxyl group so that the nick cannot be sealed by a DNA ligase. The nicked DTO has a sequence tag A, a uracil nucleotide on each of its two strand, a sequence tag B, and a 3'dC overhang.

Ligation of DTOs and Large DNA Fragments ligation of nicked DTO sequences to large DNA fragments is proceeded as described in Example 4. Since the nick has a 5' and 3' OH group, the nick cannot be sealed during the ligation and the nick is kept intact after the ligation.

Nick Translation and Self-Ligation to Generate Circular Mate Pair DNAs

The purified large circular DNA-DTO molecule is incubated with *E. coli* DNA polymerase I and a dNTP mixture. The DNA polymerase I elongates the 3' terminus of the nick, removes nucleotides from 5'->3', replaces them with dNTP and shifts the "nick" away from the original location. The distance that the nick moves along a DNA strand depends on the processivity of the DNA polymerase I. The amount of DNA polymerase I, incubation temperature, and incubation time can be optimized to extend 100 to 200 nucleotides from each nick site. Stop nick translation by inactivating DNA polymerase I and remove the enzyme and free dNTP from the nicked DNA using AMPure XP beads. Add T7 exonuclease for controlled time period to generate a gap at the nick site. Use S1 nuclease to break the large circular DNA-DTO at the newly formed gap position to generate small DNA fragments. The small DNA fragments are end repaired to generate blunt ended DNA using a NEB End repair module. After end repair, the small DNA fragments are incubated with T4 DNA ligase to form self-ligation products. The small circular DNA treated with exonuclease V and are further purified using AMPure XP beads.

PCR Amplification to Generate Linear Mate Pair DNA

Incubate the small circular DNAs with UDG and endonuclease VIII to generate a break at the location of a uracil nucleotide. Perform 5 to 15 cycles of PCR to amplify DNAs between sequence tags A and B. If needed, size selection and purification of linear mate pair DNAs can be performed on an agarose gel.

Example 5

Figure 5:
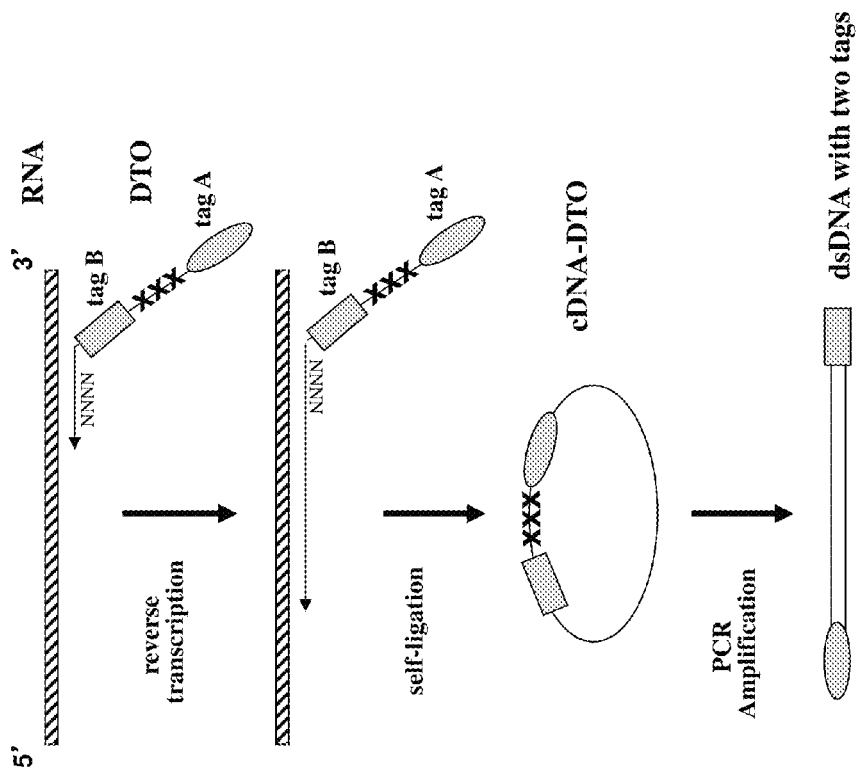
FIG. 5. A schematic illustration of making double-tagged DNA molecules from RNA molecules using random priming sequences.

Method for Making a Di-tagged DNA Library from a RNA Sample Using Random Hexamers as a Priming Sequence The method of the invention can be applied to make double-tagged DNA libraries from a RNA or DNA sample. The double-tagged DNA libraries can be used for cloning into a vector, generating hybridization probes, in vitro transcription, high throughput sequencing, and other applications. This example illustrates the procedure for making di-tagged DNA libraries from a RNA sample suitable for high throughput sequencing (FIG. 5).

Starting Materials

The starting materials for making a di-tagged DNA library can be total RNA, mRNA, rRNA depleted RNA, and small RNA isolated from cells or tissues. The method of the invention is especially effective for preparing di-tagged DNA libraries from small amounts of RNA samples when the resources are scarce such as RNA samples extracted from those associated with RNA binding proteins in CLIP assays, RNA samples isolated from small quantities of cells, or RNA samples purified from biopsies.

When using random hexamers as the priming sequence, it is possible to directly use full length RNAs as templates to generate cDNA fragments with size distributions (e.g. 200 to 500 bp) suitable for high throughput sequencing. Random hexamer primers can anneal to any complementary location on the full length RNA and initiate a cDNA synthesis. Using high primer to RNA ratio (e.g. 250 ng random hexamer per 5 µg RNA), the production of small size cDNA (<500 bp) by reverse transcription is favored. Alternatively, full length RNA molecules are fragmented into desired sizes using methods well known in the art. The fragmented and purified RNA can then be used as starting materials for making di-tagged DNA libraries.

Reverse Transcription to Synthesize cDNAs

A single-stranded DTO having, from 5' to 3', a sequence tag A, a stretch of five tetrahydrofuran abasic nucleotides, a sequence tag B, and a random hexamer is used as a primer and purified RNAs (fragmented or unfragmented) are used as templates for cDNA synthesis according to a reverse transcription protocol from New England BioLabs (Ipswich, Mass.). Briefly, 10 µM DTOs mixed with 50 to 200 ng mRNA and a dNTP mixture (1 mM of each dNTP) in RNAse-free water is heated for 3 to 5 minutes at temperature 65 to 75° C. to denature the RNA. Briefly spin down the RNA/DTO solution and promptly put it in ice. Add RNase inhibitor, a reverse transcriptase, and 10× reverse transcription buffer to the RNA/DTO solution and incubate for 45 to 60 minutes at recommended temperatures to synthesis cDNAs. After the synthesis of cDNA sequences, cDNA-DTOs are purified using AMPure XP beads (Beckman Coulter, Brea, Calif.) to remove enzymes, free NTPs and free DTO (<100 bp). RNA templates are later removed by RNase A and RNase H incubation. The single-stranded cDNAs are purified using Zymo DNA clean and concentrator kit (Zymo Research Corporation, Irvine, Calif.).

Self-ligation to Add a 3' End Sequence Tag

Purified single stranded cDNAs with DTO at its 5' end are self-ligated using CircLigase™ (Illumina, San Diego, Calif.) according to manufacturer's instruction. The resulting circularized cDNA has sequence tags A and B at its 3' and 5' ends, respectively.

PCR Amplification to Generate dsDNAs with Two Sequence Tags

The circularized cDNAs are purified and recovered using a Zymo DNA clean and concentration kit. Using primers corresponding to sequence tags A and B, the circularized cDNAs are amplified to make linear double-tagged dsDNAs. The stopping sequence between the sequence tags A and B lacks base-pairing ability with any natural nucleobases and is used to prevent DNA polymerase from extending nucleotide polymerization beyond sequence tag A or B. The stopping sequence prevents rolling cycle amplification during PCR and leads to a linear tagged dsDNA with a clean background.

Example 6

Figure 6:
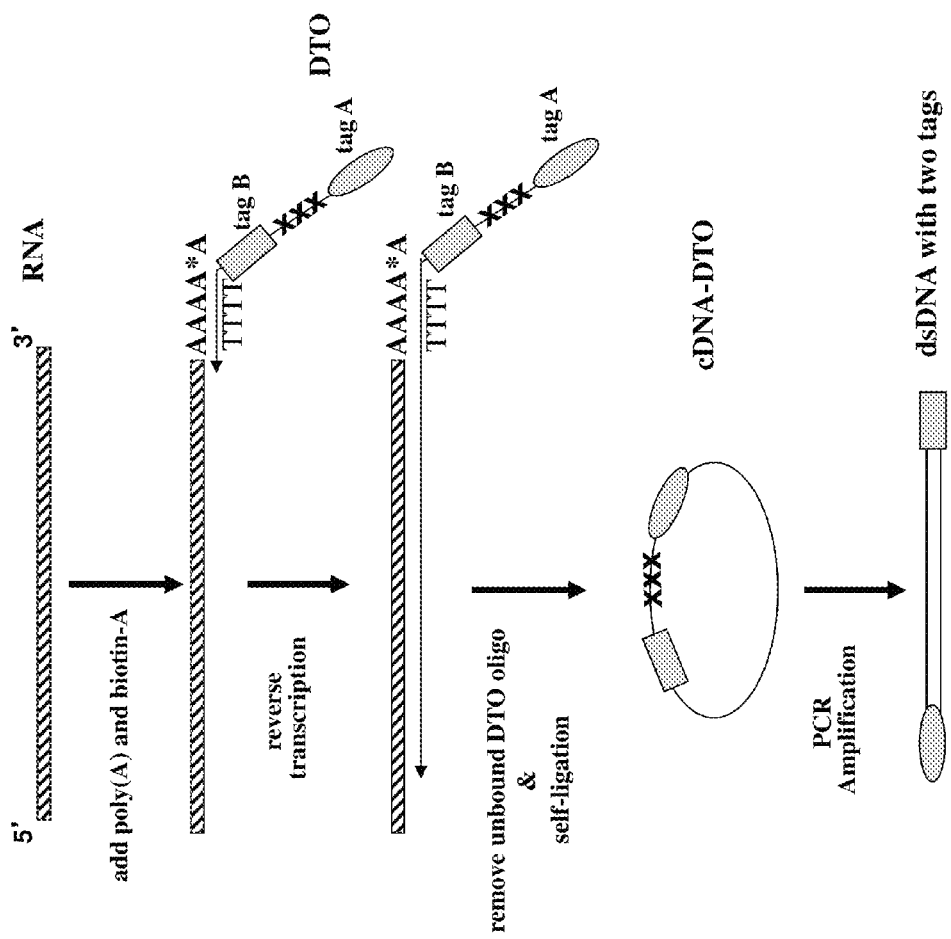
FIG. 6. A schematic illustration of making double-tagged DNA molecules from biotinylated RNA molecules.
Figure 7:
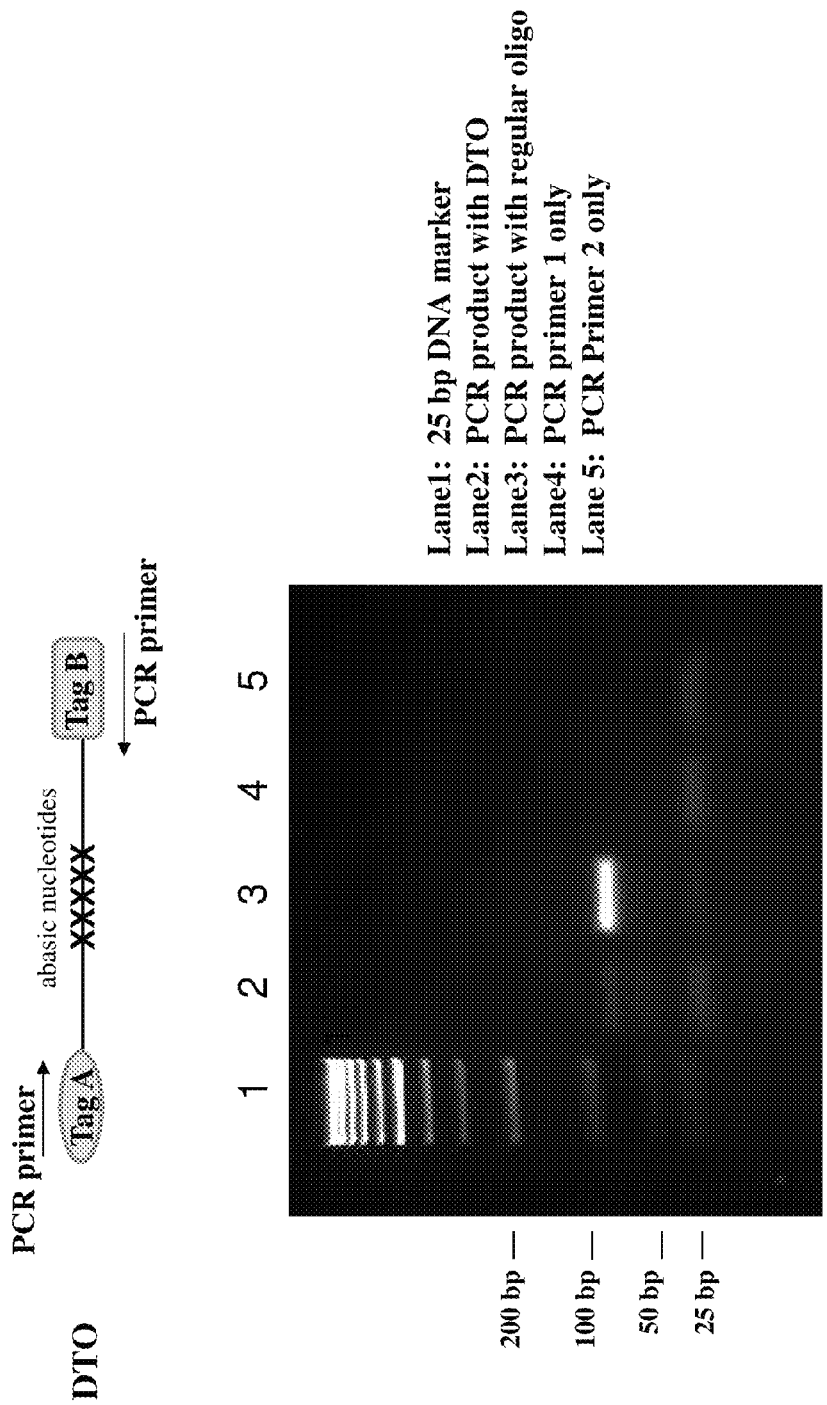
FIG. 7. Shows that DTOs prevent polymerase from reading through the stopping sequence.

Method for Making a Di-tagged DNA Library from a RNA Sample Using poly(dT) as a Priming Sequence The method of the invention can be applied to make a di-tagged DNA library from small RNA fragments using a poly(dT) tail as the priming sequence of a DTO. Using six random hexamer as a priming sequence, cDNA synthesis can be started in any location of a RNA template. Using poly(dT) as the priming sequence in the DTO ensures that the 3' end sequence of a RNA template is included in the cDNA sequence. This method is applied to small RNA sequences that have already fragmented, purified, and end repaired. It can be used for deep sequencing of whole transcriptome or quantitating mRNA expression. The poly(dT) tail contains at least 10, preferably 15 to 20, dTMPs in its sequence. Compared to random hexamer priming, priming with poly(dT) tail provides a higher priming specificity and efficiency (FIG. 6).

If quantitating of RNA expression is needed, RNA fragments do not need to be added a poly (A) tail. Only RNA fragments with a natural poly(A) tail will be reverse transcribed into cDNAs. If deep sequencing is needed, purified RNA fragments are incubated with a poly(A) polymerase in the presence of ATP and biotin-ATP according to manufacturer's instruction (NEB, Ipswich, Mass.). The tailing length and biotin density can be controlled by optimizing the reaction time, the ATP/biotin-ATP ratio and the total ATP concentration. The biotinylated poly(A)-RNAs are reverse transcribed to cDNAs using poly(dT) of DTOs as primers. The biotin-RNA/cDNA hybrids are pulled down by streptavidin-coated magnetic beads and the streptavidin beads are washed three times to remove unbound DTOs. Subsequent RNase treatment, self-ligation, and PCR amplification are proceeded as described above.

Example 7

Method for Making a Single-stranded DNA from Double-stranded DNA

This example shows a method of using a nicked DTO to make a di-tagged single-stranded DNA from a dsDNA (FIG. 9). The nicked DTO sequence used in this example has only one nick in one of the two strands, wherein the nick has a 5' and 3' hydroxyl group so that the nick cannot be sealed by a DNA ligase. The nicked dsDTO has a sequence tag A, a uracil nucleotide on the un-nicked strand (as a breaking site), a sequence tag B, and a 3' dC overhang.

Ligation of Nicked DTO and dsDNA

Ligation of nicked DTO sequences to large DNA fragments to form a nicked circular DNA-DTO molecule is proceeded as described in Example 3. Since the nick has a 5' and 3' OH group, the nick cannot be sealed during the ligation and the nick is kept intact after the ligation.

Removal of One DNA Strand Using T7 exonuclease

Incubate T7 exonuclease and exonuclease I with the circular dsDNA-DTO to remove the nicked strand of the circular DNA-DTO and other linear dsDNAs. T7 exonuclease initiates nucleotide removal at nicked site from 5'->3', and it removes mononucleotides from a dsDNA with both 5' phosporylated and unphosphorylated end. T7 exonuclease also degrades one strand of linear dsDTO and dsDNA from 5'->3', leaving undigested single-stranded DNAs that can be further digested by exonuclease I. After the exonuclease digestion, denature and remove T7 exonuclease and exonuclease I using phenol chloroform extraction and ethanol precipitation.

Generation of Linear Single-stranded DNA with Two Tags

The purified circular single-stranded DNA-DTO product is linearized by incubating with UDG and endonuclease VIII according to the protocol of NEB. The combination of UDG and endonuclease VIII generates a break at the position of Uracil nucleotide and releases a linear DNA with sequence tags A and B at its ends. Further PCR amplification can be performed if needed.

* * *

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method of making a di-tagged single-stranded DNA from a double-stranded DNA, said method comprising the steps of:
   a) providing a double-stranded double-tagged oligonucleotide (DTO) sequentially comprising a sequence tag A, a breaking site, a sequence tag B, and a single nick or gap in one of the two strands;
   b) ligating two ends of said double-stranded DNA to said double-tagged oligonucleotide to generate a circular DNA-DTO;
   c) removing the nicked/gapped strand using an exonuclease to generate a circular single-stranded DNA;
   d) breaking said circular single-stranded DNA at said breaking site to generate a linear di-tagged single-stranded DNA.

2. The method of claim 1, wherein said exonuclease comprises T7 exonuclease and exonuclease I.

3. The method of claim 1, wherein said breaking site comprises a uracil nucleotide.

4. The method of claim 1, further comprising performing a single primer PCR to amplify said di-tagged single-stranded DNA.

* * * * *